United States Patent
Dikshit et al.

(10) Patent No.: US 9,206,155 B2
(45) Date of Patent: Dec. 8, 2015

(54) CHIRAL 1-(4-METHYLPHENYLMETHYL)-5-OXO-{N-[3-T-BUTOXYCARBONYL-AMINOMETHYL)]-PIPERIDIN-1-YL-PYRROLIDINE-2-CARBOXAMIDES AS INHIBITORS OF COLLAGEN INDUCED PLATELET ACTIVATION AND ADHESION

(75) Inventors: Dinesh Kumar Dikshit, Lucknow (IN); Madhu Dikshit, Lucknow (IN); Tanveer Irshad Siddiqui, Lucknow (IN); Anil Kumar, Lucknow (IN); Rabi Sankar Bhatta, Lucknow (IN); Girish Kumar Jain, Lucknow (IN); Manoj Kumar Barthwal, Lucknow (IN); Ankita Misra, Lucknow (IN); Vivek Khanna, Lucknow (IN); Prem Prakash, Lucknow (IN); Manish Jain, Lucknow (IN); Vishal Singh, Lucknow (IN); Varsha Gupta, Lucknow (IN); Anil Kumar Dwivedi, Lucknow (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 13/995,336

(22) PCT Filed: Jan. 12, 2012

(86) PCT No.: PCT/IN2012/000032
§ 371 (c)(1),
(2), (4) Date: Jun. 18, 2013

(87) PCT Pub. No.: WO2012/104866
PCT Pub. Date: Aug. 9, 2012

(65) Prior Publication Data
US 2013/0338193 A1     Dec. 19, 2013

(30) Foreign Application Priority Data
Jan. 31, 2011 (IN) .............................. 208/DEL/2011

(51) Int. Cl.
*C07D 401/06* (2006.01)
*C07B 53/00* (2006.01)

(52) U.S. Cl.
CPC .............. *C07D 401/06* (2013.01); *C07B 53/00* (2013.01)

(58) Field of Classification Search
CPC ..................................................... C07D 401/06
USPC ........................................... 546/208; 514/326
See application file for complete search history.

(56) References Cited

U.S. PATENT DOCUMENTS 7,517,532 B2 *   4/2009   Wai et al. ................... 424/208.1

FOREIGN PATENT DOCUMENTS

| IN | 192822 | * 11/2001 |
| IN | 234205 | * 11/2001 |

OTHER PUBLICATIONS

Dikshit et al. "Process for the preparation . . . " CA145:15259 (2006).*
Slee et al. "2-amino-n-pyrimidin . . . " J. Md. Chem. 51, p. 1730-1739, CA148 structure, (2008).*
Sekhon "Eantiosepartion of . . . " Int. J. Pharm Tech Res v.2, p. 1584-1594 (2010).*
Dikshit et al. CA145 (2006).*
Dikshit et al. CA147 (2007).*
Gresele et al. "Antiplatelet Agents" p. 87-97 (2012).*

* cited by examiner

*Primary Examiner* — Celia Chang
(74) *Attorney, Agent, or Firm* — Abelman, Frayne & Schwab

(57) ABSTRACT

Chiral 1-(4-methylphenylmethyl)-5-oxo-{N-[(3-t-butoxy-carbonyl-aminomethyl)]-piperidin-1-yl}-pyrrolidine-2-car-

Figure 1:
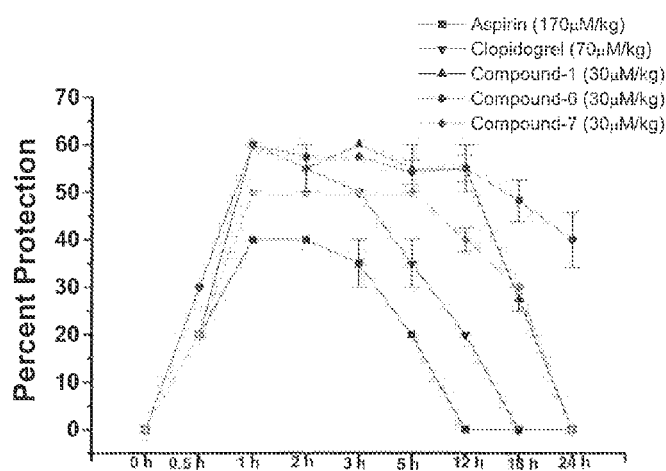

| | ADP | Collagen | Thrombin |
|---|---|---|---|
| | | PERCENT INHIBITION | |
| HCHF+ASPIRIN | 15.74±2.4 | 2.4±2 | 0.33±0.2 |
| HCHF+CLOPIDOGREL | 35±7.6 | 23.1±7.8 | 29.63±9.2 |
| HCHF+ Compound -6 | 5.6±2.7 | 34.4±6.9 | 11.4±5.6 |
| HCHF+ Compound -7 | 4.4±4.4 | 21.5±4.9 | 3.14±1.8 | boxamides as inhibitors of collagen induced platelet activation and adhesion The present invention provides chiral (2S)-1-(4-methyl-phenylmethyl)-5-oxo-(3S)—{N-[(3-t-butoxycarbonyl aminomethyl)]-piperidin-1-yl}-pyrrolidine-2-carboxamide, and (2S)-1-(4-methylphenylmethyl)-5-oxo-(3R)—{N-[(3-t-butoxycarbonyl amino methyl)]-piperidin-1-yl}-pyrrolidine-2-carboxamide of formula 6 and 7 respectively. The present invention also relates to use of these moieties as inhibitors of collagen induced platelet adhesion and aggregation mediated through collagen receptors. The present invention provides a process for preparation of chiral carboxamides of formula 6 and 7 using the process which has advantage to avoid any racemization at the a-carboxylic center, during N-alkylation. The reagent LiHMDS is used at low temperatures to furnish methyl N-(p methylphenylmethyl)lpyroglutamate in good chiral purity.

Compound 1

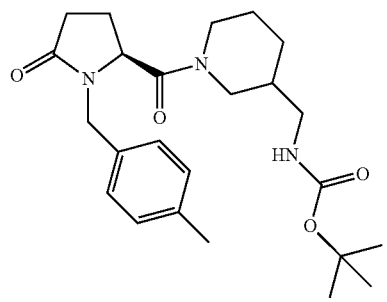

Compound 6

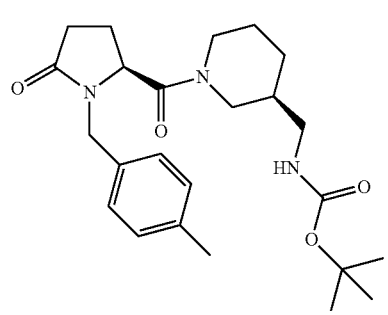

Compound 7

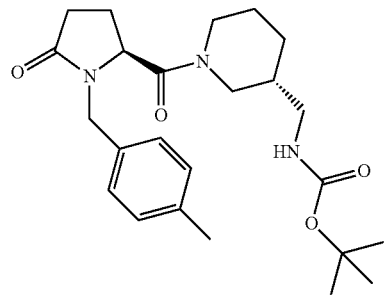

13 Claims, 22 Drawing Sheets

| Time (hrs) | Aspirin (170μM/kg) | Clopidogrel (70μM/kg) | Compound-1 (30μM/kg) | Compound-6 (30μM/kg) | Compound-7 (30μM/kg) |
|---|---|---|---|---|---|
| | | | PERCENT PROTECTION | | |
| 0 | 0±0 | 0±0 | 0±0 | 0±0 | 0±0 |
| 0.5 | 20±0 | 30±0 | 20±0 | 30±0 | 20±0 |
| 1 | 40±0 | 60±0 | 60±0 | 60±0 | 50±0 |
| 2 | 40±0 | 55±5 | 55±5 | 57.5±0 | 50±0 |
| 3 | 35±5 | 50±0 | 60±0 | 57.5±0 | 50±0 |
| 5 | 20±0 | 35±5 | 55±5 | 54.2±2.5 | 50±0 |
| 12 | 0±0 | 20±0 | 55±5 | 55±2.8 | 40±2.5 |
| 18 | 0±0 | 0±0 | 27.5±2.5 | 48.2±4.46 | 30±0 |
| 24 | 0±0 | 0±0 | 0±0 | 40±5.8 | 0±0 |

Fig: 1

| Time (hrs) | Aspirin (170μM/kg) | Clopidogrel (70μM/kg) | Compound-1 (30μM/kg) | Compound-6 (30μM/kg) | Compound-7 (30μM/kg) |
|---|---|---|---|---|---|
| | BLEEDING TIME (in Minutes) | | | | |
| 0 | 0±0 | 0±0 | 0±0 | 0±0 | 0±0 |
| 0.5 | 9.3±0.3 | 9.3±0.3 | 3.67±0.3 | 3.67±0.3 | 3.67±0.3 |
| 1 | 9±0 | 9.5±0.4 | 6.62±0.24 | 6.43±0.3 | 6.4±0.28 |
| 8 | 7.67±0.3 | 9±0.12 | 6.3±0.21 | 5.67±0.3 | 6.67±0.3 |
| 12 | 6.67±0.3 | 8±0.3 | 5.5±0.22 | 5.3±0.3 | 5.67±0.3 |
| 24 | 5.67±0.3 | 3.67±0.3 | 5±0.26 | 4.3±0.3 | 4.67±0.3 |

| | Collagen induced Platelet Aggregation | |
|---|---|---|
| Conc. (μM) | PERCENT INHIBITION | |
| | Compound-6 | Compound-7 |
| 3 | 15.44±6.1 | 15.5±7.14 |
| 10 | 48.83±3.76 | 30.1±9.5 |
| 30 | 72.2±6.7 | 73.9±9.9 |
| 100 | 91.2±3.13 | 95±3.2 |

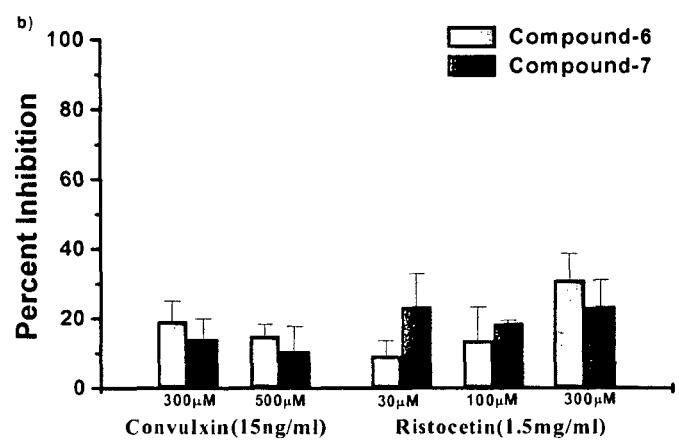
| | Convulxin induced Platelet Aggregation | |
|---|---|---|
| Conc. (µM) | PERCENT INHIBITION | |
| | Compound-6 | Compound-7 |
| 300 | 19.17±5.83 | 14.15±5.85 |
| 500 | 15.005±3.33 | 10.56±7.22 |
| | Ristocetin induced Platelet Aggregation | |
| Conc. (µM) | PERCENT INHIBITION | |
| | Compound-6 | Compound-7 |
| 30 | 9.3±4.4 | 23.28±9.58 |
| 100 | 13.7±9.58 | 18.5±0.96 |
| 300 | 30.96±7.67 | 23.3±7.67 |
Fig 3 a (ii)

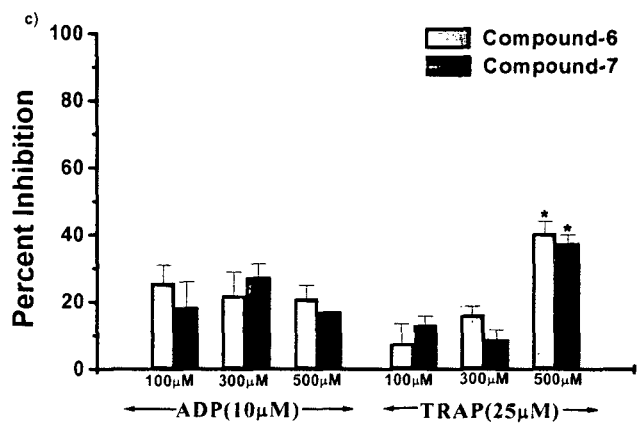
|  | ADP induced Platelet Aggregation | |
|---|---|---|
| Conc. (μM) | PERCENT INHIBITION | |
|  | Compound-6 | Compound-7 |
| 100 | 25.67±5.36449 | 18.333±7.7 |
| 300 | 22±7 | 27.3±4 |
| 500 | 21±4 | 17±0 |
|  | TRAP induced Platelet Aggregation | |
| Conc. (μM) | PERCENT INHIBITION | |
|  | Compound-6 | Compound-7 |
| 100 | 7.65±5.93205 | 13.15±2.65283 |
| 300 | 16.15±2.6056 | 8.85±2.90215 |
| 500 | 40.525±3.55583 | 37.575±2.58791 |
Fig 3a(iii)

| Compound -6 Dose (μM/kg) | | Collagen | ADP | Thrombin |
|---|---|---|---|---|
| | | PERCENT AGGREGATION | | |
| 0 | | 42.91±5.8 | 35±2.6 | 47.5±2.5 |
| 10 | | 43.75±1.25 | 43.75±3.75 | |
| 30 | | 32.5±0.72169 | 37.5±6.25 | |
| 100 | | 5±1.5 | 30±5 | 45.625±4.375 |
| 300 | | 3.125±0.76 | 28.125±3.125 | 45±1.25 |

|  | ADP | Collagen | Thrombin |
|---|---|---|---|
|  | PERCENT INHIBITION | | |
| HCHF+ASPIRIN | 15.74±2.4 | 2.4±2 | 0.33±0.2 |
| HCHF+CLOPIDOGREL | 35±7.6 | 23.1±7.8 | 29.63±9.2 |
| HCHF+ Compound -6 | 5.6±2.7 | 34.4±6.9 | 11.4±5.6 |
| HCHF+ Compound -7 | 4.4±4.4 | 21.5±4.9 | 3.14±1.8 |

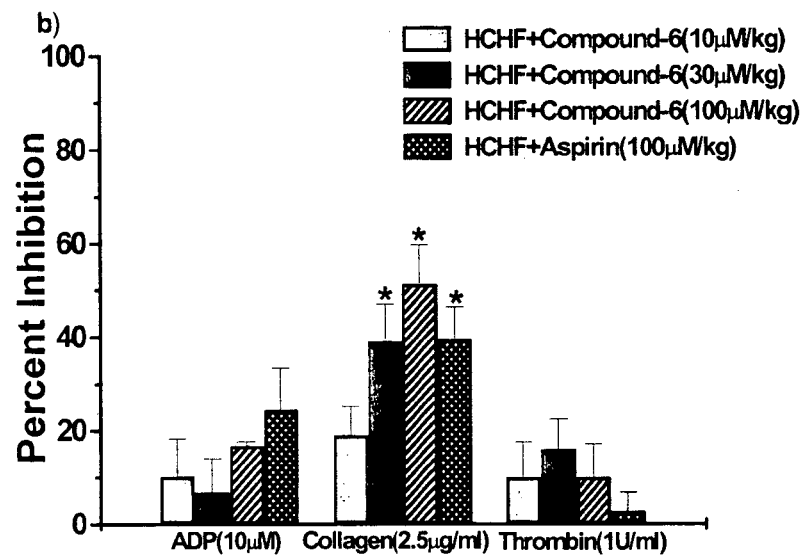
| | ADP | Collagen | Thrombin |
|---|---|---|---|
| | PERCENT INHIBITION | | |
| HCHF+ Compound -6 (10µM/kg) | 10.2±8.0 | 19±6.1 | 10±7.5 |
| HCHF+ Compound -6 (30µM/kg) | 6.8±7.2 | 39.0±8 | 16.0±6.3 |
| HCHF+ Compound -6 (100µM/kg) | 16.8±0.8 | 51.2±8.4 | 10.0±7.0 |
| HCHF+Aspirin (100µM/kg) | 24.5± 8.8 | 39.6± 7 | 4±2.8 |
Fig 3c(ii)

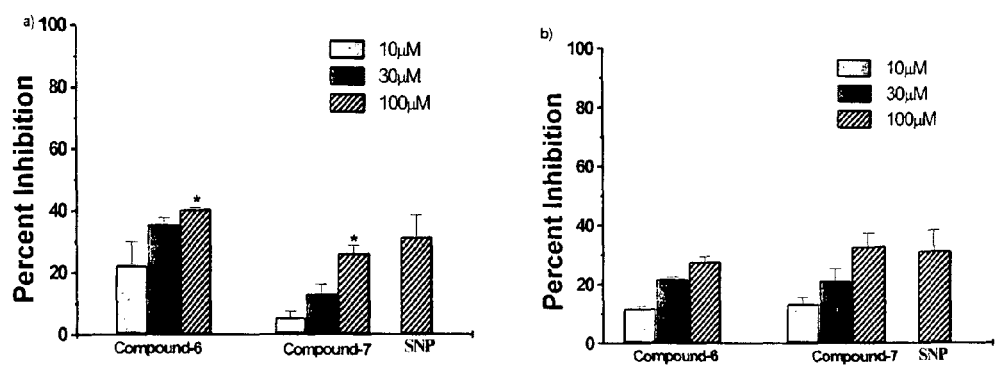
Fig 4a(i)                    Fig 4a(ii)

| Aspirin (30μM/kg) | Clopidogrel (30μM/kg) | Compound -7 (30μM/kg) | Compound -6 (30μM/kg) |
|---|---|---|---|
| PERCENT INHIBITION IN PLATELET ADHESION ||||
| 0.83±0.053 | 63±4 | 0.7±0.06 | 33±7.5 |

Figure 4B:
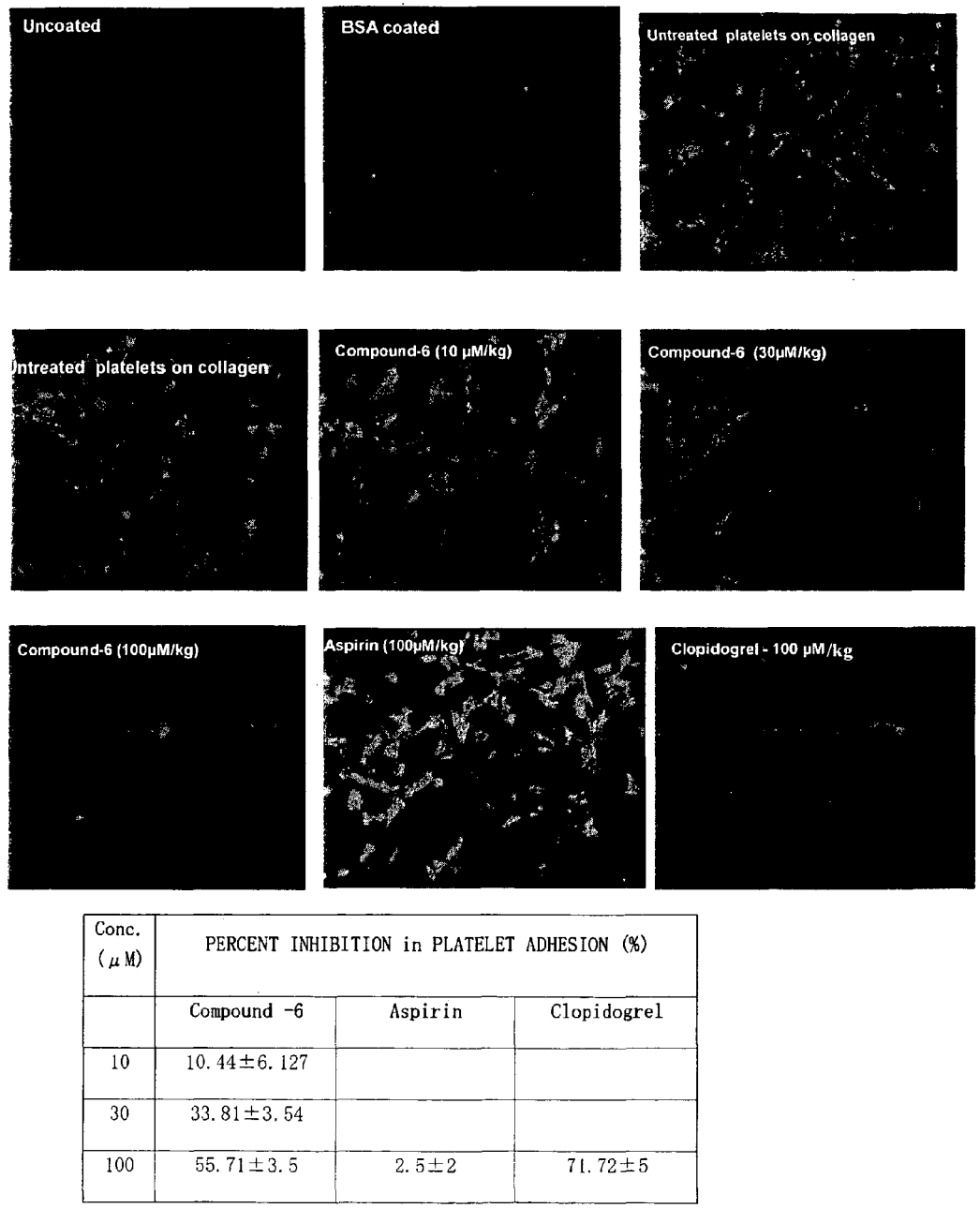
Figure 4C:
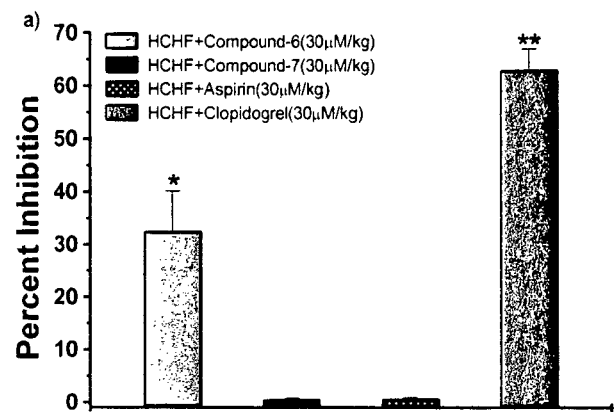

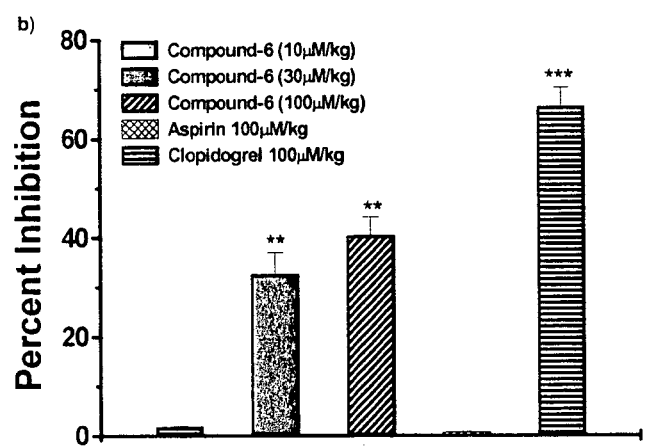
| Aspirin (100μM/kg) | Compound -6 (10μM/kg) | Compound -6 (30μM/kg) | Compound -6 (100μM/kg) | Clopidogrel (100μM/kg) |
|---|---|---|---|---|
| PERCENT INHIBITION IN PLATELET ADHESION | | | | |
| 0.7±0.06 | 1.83±0.076 | 32.71±4.3 | 40.5±3.7 | 66.4±3.86 |
Fig 4c(ii)

| Concentration | Compound -1 | Compound -6 | Compound -7 |
|---|---|---|---|
| | Percent Inhibition | | |
| 100µM | 23.5±7.8 | 7.3± 4.0 | 12.7± 10.3 |
| 300µM | 35.1±8 | 15.7± 5.2 | 25.7± 4 |
| 1mM | 53±6 | 16.7± 5.2 | 42.3± 7.5 |

| V | Aspirin (170μM/kg) | Clopidogrel (50μM/kg) | Compound-7 (30μM/kg) | Compound-6 (30μM/kg) |
|---|---|---|---|---|
| THROMBUS WEIGHT (mg/kg) | | | | |
| 51.21 ±3.799 | 25.37 ±1.647 | 23.87± 1.342 | 35.55 ±2.493 | 31.21± 3.602 |
| | | | | |

Figure 6A:
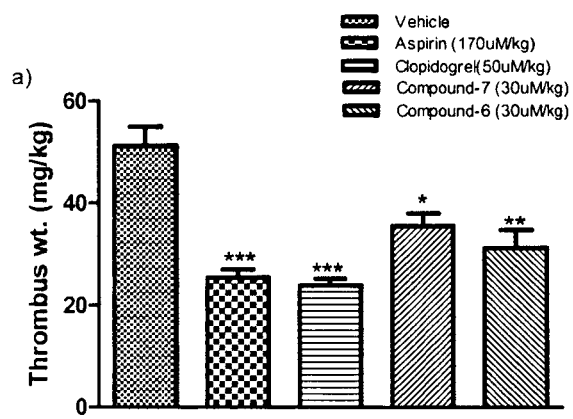

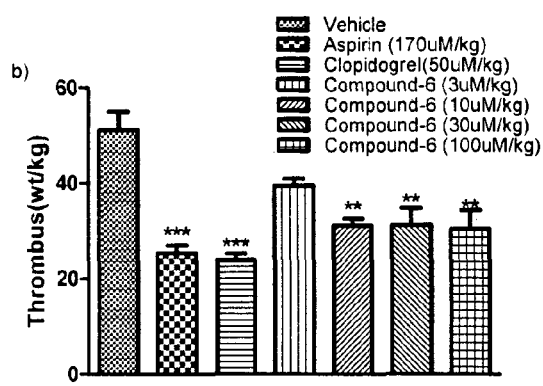
| Vehicle | Aspirin (170 μM/kg) | Clopidogrel (50 μM/kg) | Compound -6 (3 μM/kg) | Compound -6 (10 μM/kg) | Compound -6 (30 μM/kg) | Compound -6 (100 μM/kg) |
|---|---|---|---|---|---|---|
| THROMBUS WEIGHT (mg/kg) | | | | | | |
| 51.21±3.8 | 25.37 ±1.6 | 23.87± 1.3 | 39.51± 1.5 | 31.19 ±1.5 | 31.21 ±3.6 | 30.46± 3.9 |
Fig 6a(ii)

| Chow | HCHF | HCHF+ Compound -6 (10uM/kg) | HCHF+ Compound -6 (100uM/kg) | HCHF+ASP (100uM/kg) | HCHF+Clopidogrel (100uM/kg) |
|---|---|---|---|---|---|
| THROMBUS WEIGHT (mg/kg) | | | | | |
| 52.14 ± 2.825 | 68.70 ± 2.573 | 52.67 ± 3.666 | 51.65 ± 0.8203 | 52.12 ± 0.7155 | 52.13 ± 1.550 |

| Aspirin (170 μM/kg) | Compound -1 (30 μM/kg) | Compound -6 (30 μM/kg) |
|---|---|---|
| Percent Increase in Time to Occlusion (TTO) | | |
| 0.12± 2.3 | 10.6±6.2 | 15.5±4 |

Figure 7A:
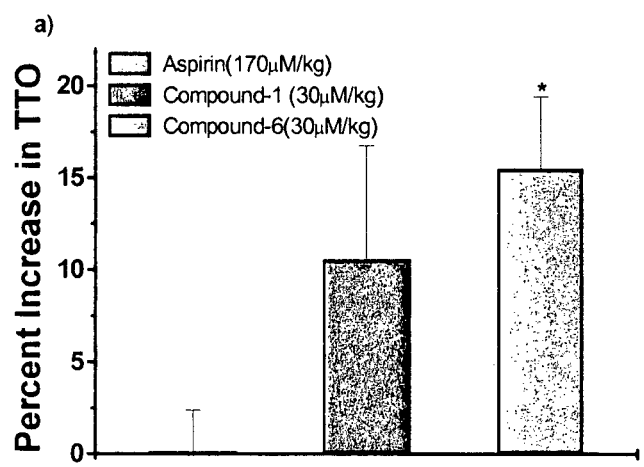

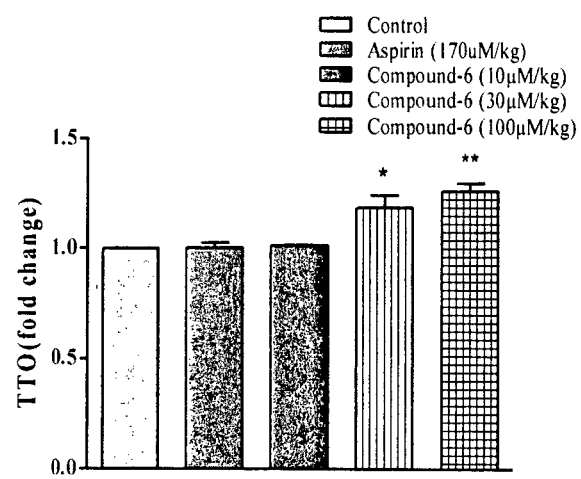
| Control | Aspirin (170μM/kg) | Compound -6 (10μM/kg) | Compound -6 (30μM/kg) | Compound -6 (100μM/kg) |
|---|---|---|---|---|
| Percent Increase in Time to Occlusion (TTO) | | | | |
| 1.00±0 | 1.004±0.02 | 1.015±0.003 | 1.2±0.06 | 1.3±0.035 |
Fig 7a(ii)

| Chow | HFD | HFD+Clopidogrel (30uM/kg) | HFD+Aspirin (30uM/kg) | HFD+ Compound -7 (30uM/kg) | HFD+ Compound -6 (30uM/kg) |
|---|---|---|---|---|---|
| Percent Increase in Time to Occlusion (TTO) | | | | | |
| 1.0± 0.0 | 0.7± 0.05 | 1.7±0.07 | 1.2± 0.02 | 1.1± 0.4 | 1.5± 0.5 |

| Time (sec) | DMSO (Vehicle) | Compound-6 (10µM) | Compound-6 (30µM) | Compound-6 (100µM) |
|---|---|---|---|---|
| | Calcium (nm) | | | |
| 300th sec | 345 | 298.4 | 226 | 144 |

CHIRAL 1-(4-METHYLPHENYLMETHYL)-5-OXO-{N-[3-T-BUTOXYCARBONYL-AMINOMETHYL)]-PIPERIDIN-1-YL-PYRROLIDINE-2-CARBOXAMIDES AS INHIBITORS OF COLLAGEN INDUCED PLATELET ACTIVATION AND ADHESION

FIELD OF THE INVENTION

The present invention relates to chiral 1-(4-methylphenyl-methyl)-5-oxo-{N-[(3-t-butoxycarbonyl-aminomethyl)]-piperidin-1-yl}-pyrrolidine-2-carboxamides. The present invention also relates to use of these moieties as inhibitors of collagen induced platelet adhesion and aggregation mediated through collagen receptors.

BACKGROUND OF THE INVENTION

Cardiovascular disease (CVD) is a major public health concern. Despite major progress in diagnosis and treatment over the years, CVD continues to represent the most frequent cause of morbidity and mortality worldwide. Platelets, which are central to normal hemostasis and limits blood loss after injury, are also the key players in pathological conditions, such as deep vein thrombosis and arterial thrombosis. They preserve vascular integrity and thereby prevent haemorrhage after injury. However, vascular damage, such as rupture of an atherosclerotic plaque, results in a platelet-dependent thrombus formation, which may lead to vascular occlusion with resultant hypoxia and infarction of distal tissues. The resulting clinical scenarios encompass stable and unstable angina, acute myocardial infarction (MI), ischaemic stroke and peripheral arterial occlusive disease.

The regulation of platelet-endothelial interaction, and thereby haemostasis and thrombosis, occurs due to precarious balance between activatory and inhibitory mechanisms that control platelet activation upon exposure to damaged tissues, yet enable platelets to remain quiescent in the undamaged circulation. In healthy vasculature, circulating platelets are maintained in an inactive state by nitric oxide and prostacyclin released by endothelial cells lining the blood vessels. Endothelial cells also express ADPase (adenosine diphosphatase), which degrades ADP released from red blood cells and activated platelets, thereby preventing further activation of platelets. When the vessel wall is damaged, the release of these endogenous anti-platelet substances is impaired and subendothelial matrix is exposed. Platelets adhere to exposed collagen and von Willebrand factor (vWF) through receptors that are constitutively expressed on the platelet surface. Adherent platelets integrate signals from the binding interaction, change their shape, secrete ADP from their dense granules, and synthesize and release thromboxane A2 (TXA2). The ADP and TXA2 that are released serve as platelet agonists by activating ambient platelets and recruiting them to the site of vascular injury. Disruption of the vessel wall also exposes platelets to collagen and tissue factor-expressing cells that further trigger the procoagulant response. In an advanced stage of activation, platelets stimulate blood coagulation by providing a surface at which the coagulation factors are activated to generate thrombin. In addition to converting fibrinogen to fibrin, thrombin also serves as a potent platelet agonist and recruits more platelets to the site of vascular injury. Activated platelets potentiate coagulation by expressing phosphatidylserine on their surface. When platelets are activated, glycoprotein (GP) IIb/IIIa (αIIbβ3), the most abundant receptor on the platelet surface, undergoes a conformational change, which increases its capacity to bind fibrinogen. Divalent fibrinogen molecules bridge adjacent platelets together to form platelet aggregates. Fibrin strands, generated by the action of thrombin, then weave these aggregates together to form a platelet-fibrin mesh.

The notion that the targeting of platelet function may be beneficial in the prevention of thrombosis is borne out by several clinical trials and the wide use of anti-platelet therapies. Anti-platelet agents can be sub classified, on the basis of their site of action, into those that inhibit (i) adhesion, (ii) activation, (iii) aggregation, or (iv) platelet-mediated links with inflammation. Of the currently available agents, aspirin, clopidogrel, dipyridamole, and cilostazol inhibit platelet activation, albeit via different mechanisms, whereas GPIIb/IIIa antagonists block platelet aggregation. However, there remains a substantial incidence of arterial thrombosis in patients on currently available anti-platelet therapy. Limitations of current therapies include weak inhibition of platelet function (for example, by aspirin), blockade of only one pathway of ADP mediated signalling (for example, by clopidogrel), slow onset of action (for example, of clopidogrel), interpatient response variability with poor inhibition of platelet response in some patients (for example, to aspirin and clopidogrel), the inability to transform the success of intravenous integrin αIIbβ3 antagonist therapy into oral therapy and the inability to completely separate a reduction in thrombotic events from an increase in bleeding events. Therefore, the successes and limitations of current therapies coupled with the advances made in our understanding of platelet biology are instructive in the design of new drugs to more effectively regulate validated targets.

Despite the complexity of extracellular matrix, platelet collagen interactions play a pivotal role in the initiation of hemostasis and thrombosis in vivo. As stable platelet adhesion and subsequent activation by collagen is mediated by platelet collagen receptors, the consequence of inhibition of either of these has gained considerable attention. Furthermore, human studies involving patients lacking either receptor, or equivalent mouse models, reveal reduced platelet responsiveness to collagen, with only mild deficiencies in haemostasis and do not lead to an increase in spontaneous bleeding tendency.

Thus, inhibition of platelet collagen-receptor activation may represent a novel pharmacological target in the search of more selective and specific antithrombotic agents for the prevention and/or treatment of acute occlusive arterial thrombosis, eg, myocardial infarction or stroke. Platelet interaction is the first step in the haemostatic process, where, extracellular matrix (ECM) is exposed at sites of injury. Among the macromolecular constituents of the ECM, collagen is considered to play a major role in this process, as in vitro it not only supports platelet adhesion through direct and indirect pathways but it also directly activates the cells in initiating aggregation and coagulant activity. The primary targets of existing anti-platelet therapy are molecules involved in platelet activation and aggregation. At present, there are no drugs in clinical use that block the initial tethering and adhesion of platelets to collagen and von Willebrand factor and hence their arrest on the blood vessel wall. The inhibition of this early step in thrombus formation is more likely to reduce or prevent the incidence of arterial thrombosis in patients of cardiovascular diseases [Review of the subject: *PNAS*, 2009 vol. 106 no. 3 719-724, *Small-molecule inhibitors of integrin α2β1 that prevent pathological thrombus formation via an allosteric mechanism*].

There have been several reports of peptide & proteins which inhibit platelet aggregation by inhibiting platelet activation by collagen & other endothelial derived activating molecules [*FEBS Journal* 277 (2010) 413-427, *Aegyptin displays high-affinity for the von Willebrand factor binding site (RGQOGVMGF) in collagen and inhibits carotid thrombus formation in vivo*; *J Thromb Thrombolysis* (2007) 24:275-282, *Inhibition of collagen, and thrombin-induced platelet* aggregation by Lansberg's hognose pit viper (*Porthidium lansbergii hutmanni*) venom; *Acta Biochimica Polonica*, Vol. 50 No. 4/2003, 1119-1128, *Inhibition of collagen-induced platelet reactivity by DGEA peptide; FEBS Journal* 273 (2006) 2955-2962, *Identification and characterization of a collagen-induced platelet aggregation inhibitor, triplatin, from salivary glands of the assassin bug, Triatoma infestans*; U.S. Pat. No. 5,851,839: Platelet aggregation inhibitors; 6 U.S. Pat. No. 5,756,454, Collagen-induced platelet aggregation inhibitor; U.S. Pat. No. 5,710,131, Inhibitor of collagen-stimulated platelet aggregation; U.S. Pat. No. 5,587,360, Platelet adhesion inhibitor].

However there are very few reports of small molecules which are capable of blocking platelet activation/aggregation by collagen & other endothelial derived activating molecules [(WO/1995/006038) Platelet aggregation inhibitors and references cited therein; U.S. Pat. No. 6,221,357, Flavonoids derived from citrus peels as collagen-induced platelet aggregation inhibitor; U.S. Pat. No. 5,814,636, Compounds with platelet aggregation inhibitor activity; U.S. Pat. No. 5,719,145, Amidine derivatives and platelet aggregation inhibitor containing the same; U.S. Pat. No. 5,698,692, Compound with platelet aggregation inhibitor activity; U.S. Pat. No. 5,629,321, Bicyclic compound and platelet aggregation inhibitor containing the same; *J. Med. Chem.* 2007, 50, 5457-5462, *Small Molecule Inhibitors of Integrin α2β1; PNAS*, 2009 vol. 106 no. 3 719-724, *Small-molecule inhibitors of integrin α2β1 that prevent pathological thrombus formation via an allosteric mechanism; Cardiovascular Research* 75 (2007) 782-792, *Characterization of a novel and potent collagen antagonist, caffeic acid phenethyl ester, in human platelets: In vitro and in vivo studies; Arterioscler Thromb Vasc Biol* 2007; 27; 1184-1190; *EXP3179 Inhibits Collagen-Dependent Platelet Activation via Glycoprotein Receptor-VI Independent of AT1-Receptor Antagonism Potential Impact on Atherothrombosis; Phytother. Res.* 16, 398-399 (2002), *Human Platelet Aggregation Inhibitors from Thyme (Thymus vulgaris* L.); *J. Med. Chem.*, 2010, 53 (5), pp 2087-2093, *Structural Basis for Platelet Antiaggregation by Angiotensin II Type 1 Receptor Antagonist Losartan (DuP-753) via Glycoprotein VI]*

Amides of N-substituted pyroglutamic acids have been reported as moderate inhibitor of thrombin (Dikshit et al., 2001 Indian Patent 1206/DEL/2001) and has shown anti-thrombotic activity in mice model of thrombosis.

Therefore, the present invention focuses on the identification and preparation of pure diastereomers of a class of compounds which specifically inhibits collagen mediated platelet aggregation without affecting other regulatory and physiologically relevant platelet functions, and thus provides a clinically useful anti-thrombotic agent. The present invention makes pure diastereomers for improvement of their activity compared to the mixture of diastereomers.

OBJECTS OF THE INVENTION

The main object of the invention is to provide the compounds which inhibit collagen induced platelet adhesion and aggregation in in vitro and ex vivo assays. Invention relates to compounds of general formula 6 and 7 which are distereomeric forms of chiral 1-(4-methylphenylmethyl)-5-oxo-{N-[(3-t-butoxycarbonyl-aminomethyl)]-piperidin-1-yl}-pyrrolidine-2-carboxamides of general formula I, wherein the general formula 1 comprising the chiral compound of formula 6 and 7.

Another object of the invention is the compounds of formula 6 and 7 individually or mixture thereof for preventing thrombosis, platelet adhesion and aggregation and useful in various cardiovascular disease states as anti-platelet compound.

Further object of the invention is to provide the compounds having prolonged duration of action against Collagen-epinephrine induced thrombosis in comparison to standard drugs such as aspirin and clopidogrel.

Still another object of the invention is to provide the compounds having significantly less prolongation of bleeding time as compared to the standard anti-platelet drugs such as aspirin and clopidogrel.

One more object of the invention is to provide the compounds having faster absorption, higher water solubility and better bio-availability.

Further object provides the process for the preparation of pure forms of compound 6 and compound 7.

Furthermore object is to provide compositions for the treatment of cardiovascular disease comprising the compound of formula 6 or 7 individually with pharmaceutically acceptable additives and excipients.

SUMMARY OF THE INVENTION

Accordingly, the present invention provides a Chiral 1-(4-methylphenylmethyl)-5-oxo-{N-[(3-t-butoxycarbonyl-aminomethyl)]-piperidin-1-yl}-pyrrolidine-2-carboxamides of general formula 1 wherein the formula 1 comprising the chiral compound of formula 6 and 7

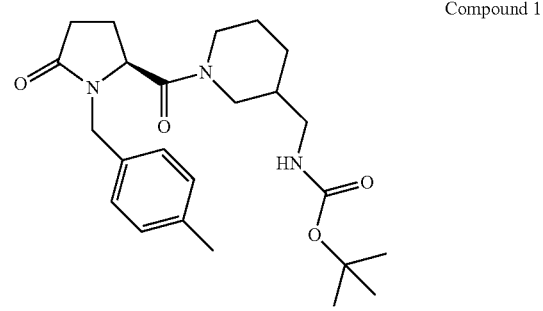

Compound 1

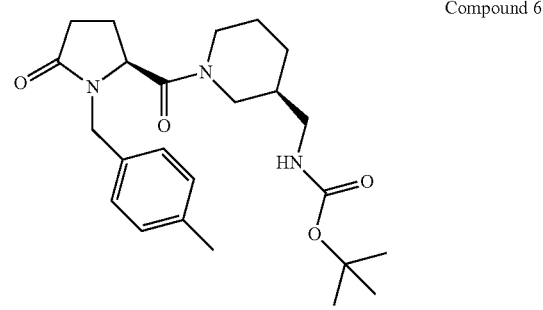

Compound 6

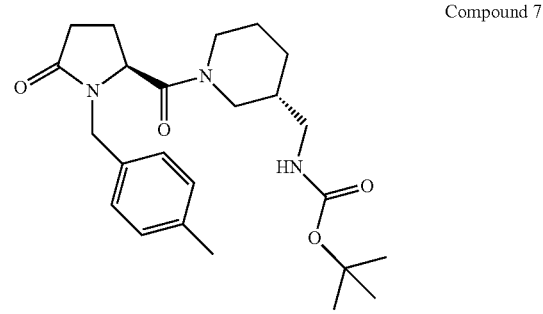

Compound 7

In an embodiment of the invention the compounds are useful for preventing thrombosis, platelet adhesion and aggregation.

The preferred embodiment of this invention provides the compound of formula 6 and 7 individually or mixture thereof for preventing thrombosis, platelet adhesion and aggregation and useful in various cardiovascular disease states as anti-platelet compound.

More preferred embodiment of this invention provides compound of formula 6 is more active with long lasting effect when compared against standard drug Aspirin and Clopidogrel as well as compound 1 and 7 in Collagen-epinephrine induced pulmonary thromboembolism in mice.

Another embodiment of this invention provides the compound 1, 6 and 7 (30 μM/kg, 1 hr p.o. dosing) exhibited a prolongation in bleeding time, which was significantly less as compared to the standard anti-platelet drug, aspirin and clopidogrel.

Yet another embodiment provides the compound 1, 6 and 7 are active against collagen induced aggregation in vitro in human platelet rich plasma while no effect on ADP induced platelet aggregation, and compound 6 and 7 are more specific than compound 1 which exhibits moderate efficacy against thrombin mimetic, SFLLRN (TRAP) induced platelet aggregation.

Yet another preferred embodiment provides compound 6 is better than compound 7 in attenuating collagen stimulated platelet aggregation in hyperlipidemic hamsters.

Another embodiment is the compound 6 exhibiting dose dependent reduction in platelet adhesion over collagen matrix and comparatively better than aspirin in mice (ex vivo).

Another embodiment is that the compound 6 is better than compound 7 in inhibiting platelet adhesion over, collagen coated surface GPVI- and α2β1-mediated platelet adhesion assay on collagen (Human, in-vitro).

In another embodiment it is discussed that in hyperlipidemic hamsters, the compound 6 exhibits significant attenuation in platelet adhesion over collagen surface in contrast to compound 7 which exhibits no effect on the same.

Further embodiment provides the compound 1 and 7 nonspecifically attenuated thrombin amidolytic activity while compound 6 did not exhibit any of such non-specific thrombin inhibitory property.

Furthermore embodiment provides the compound 6 significantly reduces thrombus weight even at 10 μM/kg in arterio-venous shunt model in rat and hyperlipidemic hamsters.

Even further embodiment provides the compound 6 significantly prolonged the time to occlude the carotid artery in rats (FeCl$_3$ induced arterial thrombosis), thus displaying its remarkable antithrombotic potential, while compound 1 failed to exhibit any protection at the same dose.

Even furthermore embodiment provides the compound 6 significantly increased the time to occlusion in hyperlipidemic hamsters, thus confirming its substantial antithrombotic efficacy in a disease model, while compound 7 remained ineffective and thus did not display antithrombotic characteristic in the same.

Further embodiment provides that the compound 6 exhibits faster absorption and prolonged systemic exposure for more than 24 hrs {$C_{max}$ (149.49±53.12), $t_{max}$ 0.75±0.144 hrs} and higher water solubility (416.41±62.35 μg/ml) when compared to compound 7 {$C_{max}$(112.81±169.77, $t_{max}$ 8.67±0.66)} and water solubility (71.75±13.45 μg/ml); and the compound 1 comparatively exhibits fast absorption leading to $C_{max}$ of 947.02±237.4 ng/ml.

Another embodiment provides the process for the preparation of compound 6 and compound 7 wherein the process steps comprising of;
reacting methylpyroglutamate with p-methyl benzyl bromide
in an aprotic solvent in presence of LiHMDS at a temperature ranging between 0 to 35° C. for a period ranging between 1 to 4 hr, quenching the reaction mixture with HCl and obtaining the compound of formula 2,

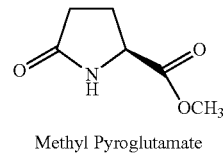

Methyl Pyroglutamate

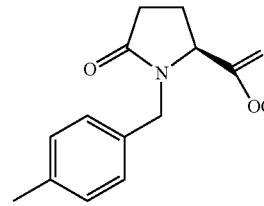

Formula 2 reacting compound of formula 2 with sodium carbonate at a temperature ranging between 0° C. to 30° C. for a period ranging between 0.5 to 4 hr to obtain (2S)—N-(p-methylphenylmethyl)pyroglutamic acid of formula 3

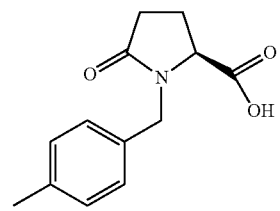

Formula 3 reacting compound of formula 3 with compound of formula 4[(3R)—N-(t-butoxycarbonyl)-3-aminomethyl-piperidine] or 5[(3S)—N-(t-butoxycarbonyl)-3-aminomethyl-piperidine] in an aprotic solvent selected from a group consisting of dichloromethane, tetrahydrofuran and dioxane, in presence of a coupling reagent selected from the group consisting of dicyclohexylcarbodiimide and benzotriazole-1-yl-oxy-tris-pyrrolidino-phosphonium hexafluorophosphate, OR an activating agent 1-hydroxy benzotrizole or isobutyl chloroformate at a temperature ranging between −20° C. to +30° C. for a period ranging from 1 to 3 hrs followed by purification using chromatography to produce compound of formula 6 or 7 respectively.

In an embodiment of the invention wherein the compound of formula 3 is reacted with oxalyl chloride at 0° C. to obtain the acid chloride followed by reaction with compound of formula 4 or 5 in presence of triethylamine in dichloromethane at room temperature for a period ranging from 2 h to 3 h to obtain the compound of formula 6 or 7 respectively.

In another embodiment of the invention wherein the compound of formula 3 is reacted with compound of formula 4 or 5 in presence of a coupling reagent dicyclohexylcarbodiimide and 1-hydroxy benzotrizole in dichloromethane at a temperature ranging between −5° C. to 0° C. for a period ranging between 2 h to 3 h to obtain compound of formula 6 or 7 respectively.

In a further embodiment of the invention wherein the compound of formula 3 is reacted with compound of formula 4 or 5 in the presence of diisopropyl ethylamine, and benzotriazole-1-yl-oxy-tris-pyrrolidino-phosphonium hexafluoro phosphate, in dichloromethane at temperature ranging between −5° C. to 00° C. for a period ranging between 2 h to 3 h followed by stirring at temperature at temperature ranging between 0° C. to 25° C. to obtain compound of formula 6 or 7 respectively.

In still another embodiment of the invention wherein the compound of formula 3 is reacted with compound of formula 4 or 5 in presence of triethyl amine, and isobutyl chlorormate, in THF at −20° C., for a period ranging between 1 h to 2 h followed by stirring at temperature at temperature ranging between 0° C. to 25° C. to obtain the compound of formula 6 or 7.

Even furthermore embodiment provides the purification of compound 6 and 7 is carried out by crystallization using the solvents selected from a group consisting of pentane, hexane, cyclohexane, toluene, ethyl acetate.

Another embodiment provides the use of said compounds 6 or 7 for treatment of coronary syndrome (ACS) such as ST-segment elevation myocardial infarction (MI), non-ST segment elevation MI, unstable angina, thrombotic stroke and in patients of angioplasty to prevent platelet activation and adhesion.

Furthermore embodiment provides compounds for the treatment of cardiovascular disease comprising the compound of formula 6 or 7 individually with pharmaceutically acceptable additives and excipients.

Furthermore embodiment provides composition wherein the pharmaceutically acceptable additive is selected form a group consisting of DMSO, gum acacia or CMC, beta cyclo-dextrin, or any other pharmaceutically acceptable excipients.

BRIEF DESCRIPTION OF DRAWINGS (*n=no. of experiments)

FIG. 1: Effect of compound 1, 6 and 7 on collagen-epinephrine induced pulmonary thromboembolism in mice in a time dependent study. Results are expressed as Mean±SEM (n=5, 10 animals/group/experiment)

Figure 2:
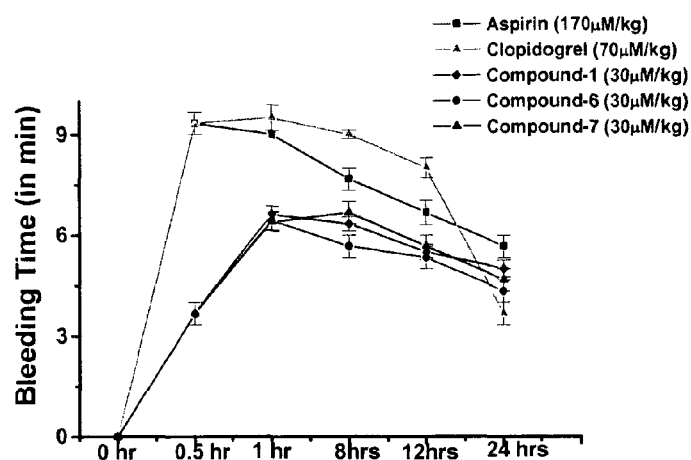

FIG. 2: Effect of compound 1, 6 and 7 on tail bleeding time in mice in a time dependent study Results are expressed as Mean±SEM (n=5, 10 animals/group/experiment).

Figure 3A:
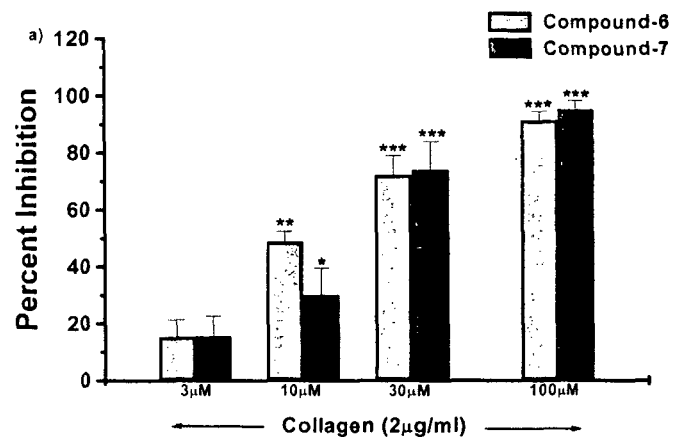

FIG. 3a: Effect of compounds 6 and compound 7 on aggregation of human platelet rich plasma (in vitro) induced by (i) Collagen (ii) Convulxin and Ristocetin (iii) ADP and TRAP. Results are expressed as Mean±SEM (n=3)

Figure 3B:
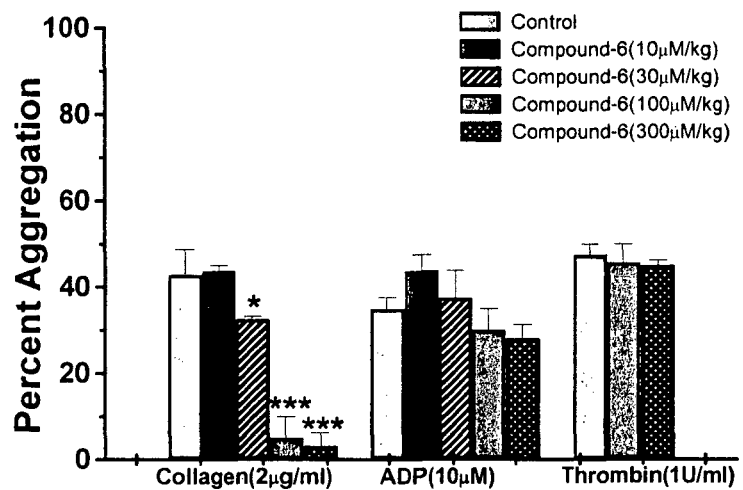

FIG. 3b: Effect of compound 6 on aggregation of mice platelet rich plasma (ex vivo) induced by Collagen, ADP and Thrombin. Results are expressed as Mean±SEM (n=5, 5 animals/group/experiment).

FIG. 3c: Whole blood aggregation responses of chow fed and high cholesterol high fat fed hamsters induced by ADP (10 μM), Collagen (2.5 μg/ml) and Thrombin (1 U/ml) (no. of animals=10/group). (i) effect of standard anti-platelet drugs and compounds 6 & 7 on whole blood aggregation (ii) effect of compound 6 on platelet aggregation in dose dependent manner (n=10, no. of animals=10/group). Results are expressed as Mean±SEM.

FIG. 4a: Effect of compounds 6 & 7 on human platelet adhesion on (a) fibrillar and (b) soluble collagen coated surface. Results are expressed as Mean±SEM (n=3).

FIG. 4b: Adhesion of mouse platelets on collagen matrix as observed under fluorescence microscope 40× (ex vivo method). Different pictures show the different treatment performed. Washed murine platelets (2×10$^6$/ml) were obtained from animals pretreated with the compound (compound 6) (different doses) and seeded on BSA or Collagen (fibrillar) coated cover slips (A, B). Platelets from untreated animals were allowed to adhere on uncoated and BSA coated cover slip respectively to delineate the possibility of non specific binding. C, D. control platelets were adhered on collagen coated cover slip (control). E, F&G. Platelets obtained from animals pre-treated with compound 6 (10 μM/kg, 30 μM/kg & 100 μM/kg) respectively were adhered on collagen coated cover slip. H, I. Platelets from Aspirin (100 μM/kg) & Clopidogrel treated (100 μM/kg) animals resp. (standard Drugs) and adhered on collagen coated cover slip (n=5, 5 animals/group/experiment).

FIG. 4c: (i) Effect of compound 6 & 7 and standard drugs on platelet adhesion (ex-vivo) in hyperlipidemic hamsters on collagen coated surface (ii) effect of compound 6 on platelet adhesion in a dose dependent-[ent way. Results are expressed as Mean±SEM (no. of animals=10/group).

Figure 5:
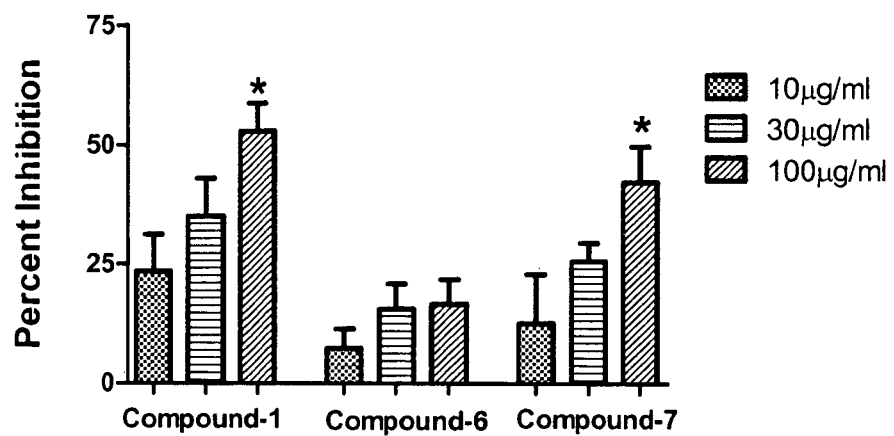

FIG. 5: Effect of compound 1, 6 and 7 on amidolytic activity of human alpha-thrombin using fluorogenic substrate. Results are expressed as Mean±SEM.

FIG. 6a: (i) Effect of compounds 6 and 7 in reducing the thrombus weight and their efficacy was compared to those of standard anti-platelet drugs, aspirin and clopidogrel in rats. (ii) Effect of compounds 6 in dose dependent manner. Results are expressed as Mean±SEM (n=3)

Figure 6B:
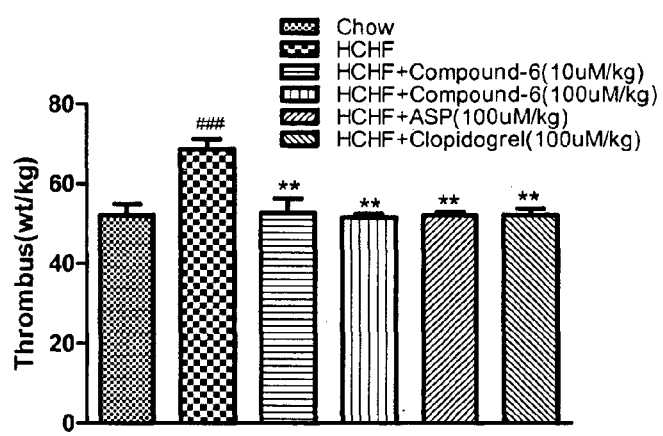

FIG. 6(b): Effect of compound 6 on High fat diet treatment which increased the thrombus weight, thus displaying a pro-thrombotic state induced by hyperlipidemic diet mimicking the clinical condition. Results are expressed as Mean±SEM (n=3).

FIG. 7a) (i) Effect of compound 6 & 7 on total time to occlusion (TTO) in ferric chloride induced arterial thrombosis in rats (n=6) (ii) Effect of compound 6 on time to occlusion (TTO) in rats in a dose dependent way. Results are expressed as Mean±SEM (no. animals=6/group).

Figure 7B:
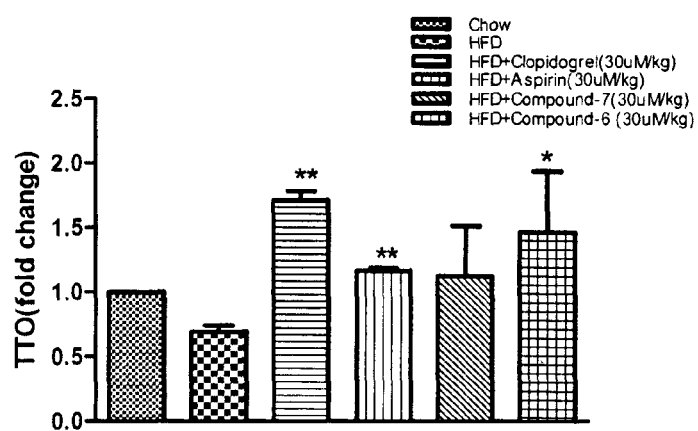

FIG. 7b: Effect of compound 6 & 7 on total time to occlusion (TTO) in ferric chloride induced arterial thrombosis in hyperlipidemic hamsters. Results are expressed as Mean±SEM (no. of animals=6/group)

Figure 8:
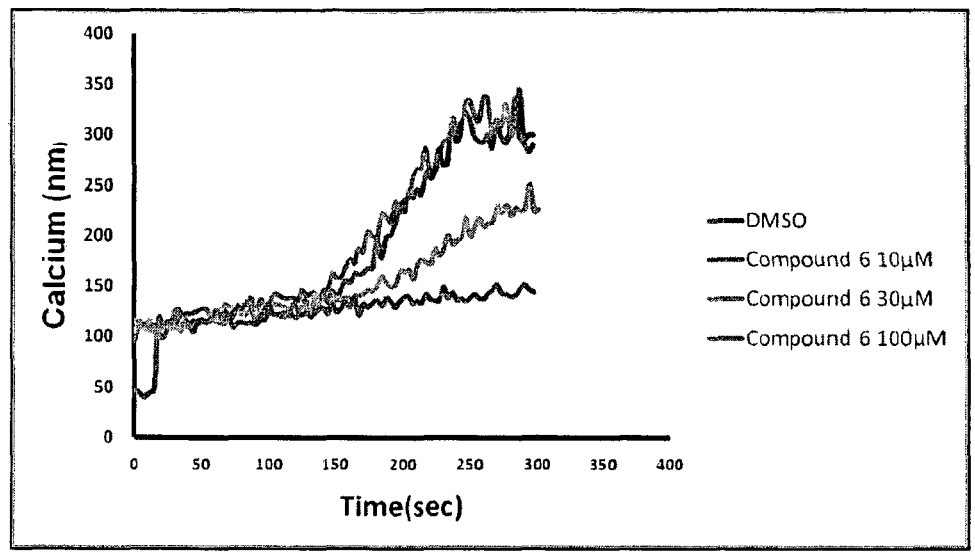

FIG. 8: Effect of compound 6 on intracellular calcium mobilization in Fura-2 loaded human platelets stimulated by collagen (5 μg/ml) (n=3)

Figure 9:
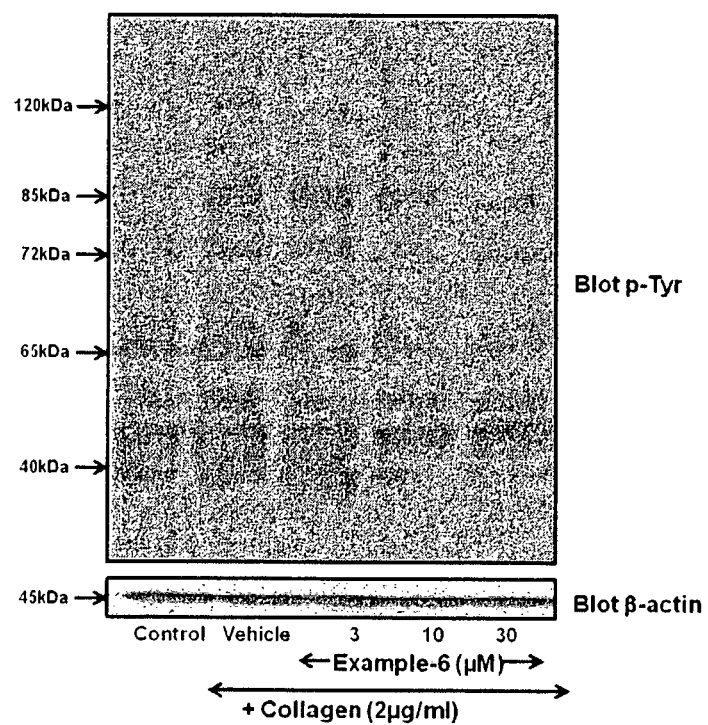

FIG. 9: Effect of compound 6 on tyrosine phosphorylation of platelet proteins after stimulation with collagen (2 μg/ml) (n=3)

Figure 10:
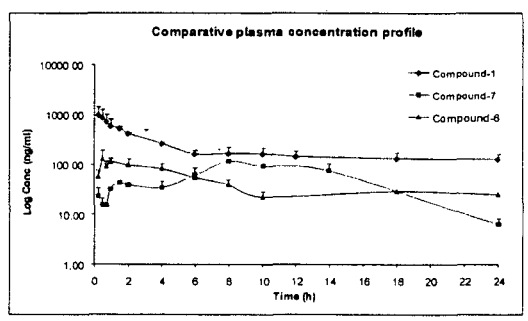

FIG. 10: Plasma concentration time profile of compound 1, 6 & 7 (n=3)

ABBREVIATIONS

ADP, adenosine diphosphate, PMA, 12-phorbol 13-myristate acetate, AA, Arachidonic Acid, TRAP, thrombin receptor activated peptide, EGTA, ethylene glycol tetra acetic acid, ACD, acid-citrate-dextrose, gp, glycoprotein, PBS, phosphate buffered saline, FeCl$_3$, ferric chloride, TTO, time to occlusion, HRP, horseradish peroxidise, CMC, carboxymethyl cellulose, PRP, platelet rich plasma, PPP, platelet poor plasma, DMSO, dimethyl sulfoxide, HEPES, (N-[2-hydroxyethyl]piperazine-N'-[2-ethanesulfonic acid]), SDS, sodium dodecyl sulphate, PMSF, phenyl methyl sulphonyl fluoride, TBST, tris buffered saline with Tween-20, p-Tyr, phospho-tyrosine BSA, bovine serum albumin, HCHF, high cholesterol high fat, SNP, Sodium Nitroprusside, μg, microgram, μM, micromolar, kDa, kilo Dalton, C$_{max}$, Maximum plasma concentration, tmax, time to achieve maximum plasma concentration, AUC, Area under curve, MRT, mean residence time LiHMDS, Lithium bis-(trymethylsilyl)amide, DIC, N,N'-Diisopropyl carbodiimide, HOBt, 1-Hydroxybenzotriazole, PyBOP, Benzotriazol-1-yl-oxytripyrrolidinophosphonium hexafluorophosphate, DCM, Dichloromethane, HPLC, High Performance Liquid Chromatography, IR, Infrared, NMR, Nuclear Magnetic Resonance spectoscopy, FAB MS, Fast Atom Bombardment Mass Spectrocopy, $Na_2SO_4$, Sodium sulphate, HCl, Hydrochloric acid, MP, melting point, $CDCl_3$, duteriated chloroform, MHz, Mega hertz, mmol, millimol, $[\alpha]_D$, Specific rotation, δ, Chemical shift, KBr, Potassium bromide

DETAILED DESCRIPTION OF THE INVENTION

Accordingly, this invention provides compounds which inhibit collagen induced platelet adhesion and aggregation in in vitro assays and ex vivo collagen induced comparative platelet adhesion assays represented by Compound 1 which as stated in the Indian patent (1206/DEL/2001) is a 1:1 mixture of diastereomers Compound 6 and Compound 7, which could not be separated by crystallization, or by chromotagraphic methods such as HPLC, more particularly, but not to be construed as limiting, the presently disclosed and claimed invention relate to the chiral synthesis of both diastereomers and the separation of biological actions in the preferred compound (Compound 1) so as to identify one of the chirally pure diastereomers (compound 6) as having superior anti-thrombotic efficacy.

The invention efficiently utilizes the tartarate salts for the chiral resolution of racemic Piperidin-3-ylmethyl-carbamic acid tert-butyl ester, similar to reported procedure (WO2006/28904 A1, 2006) to obtain 3S or 3R piperidin-3-ylmethyl-carbamic acid tert-butyl ester.

N-p-methyl-phenylmethyllpyroglutamic acid was prepared according to the literature reported protocol described in the experimental section.

In an inventive step, to avoid any racemization at the α-carboxylic center, during N-alkylation, the reagent LiHMDS at low temperatures is claimed to furnish Methyl N-p-methyl-phenylmethyllpyroglutamate in good chiral purity.

To avoid any racemization at the α-carboxylic center, for example, during coupling process, very efficient and mechanism specific coupling agents are generally used as DCC with HOBt or PyBOP in dry DCM, but this may not preclude the use of simple acid chloride mediated couplings, as the invention provides compounds in microcrystalline form and repeated crystallization may afford these compounds in almost 99% chiral purity (chiral HPLC), as otherwise indicated.

Asprin and clopidogrel are used as standard drugs and gum acacia, CMC as vehicles.

The invention utilizes a mouse model of collagen-epinephrine induced pulmonary thrombombolism and bleeding time to justify the effectiveness (for a extended period) of compound 6 over its analog compound 7 and their diastereomeric mixture, compound 1 (FIG. 1, 2).

The invention discusses the studies detailing the anti-adhesive/anti-aggregating activities of two compounds (6 & 7) in various in-vitro/ex-vivo/in-vivo models manifesting better pharmacological and pharmacokinetic profile over the diastereomeric mixture, compound 1.

The invention includes compound 1, 6 and 7 to be active against collagen induced aggregation in vitro in human platelet rich plasma. The in vitro anti-aggregatory activity was comparable among all the three compounds as they inhibited collagen mediated effects at similar concentrations (FIG. 3a).

Further, the invention includes compounds 6 and 7 not to exhibit any effect on ADP, Ristocetin and thrombin mimetic, SFLLRN (TRAP) induced platelet aggregation, while the diastereomeric mixture, Compound 1, exhibited a significant inhibition against TRAP induced platelet aggregation, thereby displaying its non-specific mode of action (FIG. 3b, c).

The invention includes compound 6, even at higher concentrations (500 μM) does not significantly inhibit platelet aggregation induced by convulxin, a GP VI receptor agonist but inhibits collagen induced aggregation (FIG. 3a).

Another preferred embodiment includes compound 6 exhibits a dose dependent reduction in collagen mediated platelet aggregation in mice when evaluated ex vivo (FIG. 3b).

Further the invention discusses measuring aspirin mediated platelet aggregation inhibition in HCHF fed Hamsters wherein aspirin can only inhibit ADP and Thrombin but not collagen induced aggregation. (FIG. 3c)

Measuring clopidogrel mediated platelet aggregation inhibition in HCHF fed Hamsters wherein the clopidogrel can only inhibit ADP induced aggregation. (FIG. 3c)

Further measuring compound 1 and 6 mediated platelet aggregation inhibition in HCHF fed Hamsters while compound 7 remained ineffective and the preferred compound (Compound 6) is claimed to significantly inhibit collagen induced platelet aggregation in high fat fed groups in a dose dependent manner (FIG. 3c).

Compound 1, 6 and 7 partially inhibited both GP VI and GP Ia IIa mediated human platelet adhesion over collagen (in vitro) while the effect was more prominent in GP VI mediated pathway (FIG. 4a).

Treatment with preferred compound 6 is claimed to significantly reduce mice platelet adhesion on collagen coated plates which are comparable to clopidogrel treatment (FIG. 4b).

Measurement of the platelet hyperactivity in HCHF fed hamsters through isolated platelet adhesion assays on both collagen and fibrinogen coated plates. The invention, Compound 1 and 6, exhibit significant reduction in platelet adhesion which are comparable to clopidogrel treatment, whilst treatment with Compound 7 and Aspirin are found insignificant in reducing platelet adhesion on the collagen coated surface in hyperlipidemic hamster model of atherosclerosis (FIG. 8a). The preferred compound 6 exhibits a dose dependent reduction in diet induced platelet hyperactivation when adhered over collagen coated surface in hyperlipidemic hamsters (FIG. 4c).

The invention, in a set of experiments describes the effect of Compound 1, 6 and 7 on amidolytic activity of human α-thrombin using fluorogenic substrate was evaluated where unlike compound 1 and compound 7, compound 6 showed negligible activity. (FIG. 5)

The invention, in general, utilizes several in vivo & ex-vivo assays to ascertain their antithrombotic potency in AV-shunt model, Ferric chloride induced carotid thrombosis, to justify the efficacy of 6 over 7 against various thrombosis models. [FIG. 6a,b, FIG. 7a,b]

The invention, in another set of experiments finds that the preferred compound (compound 6) inhibits collagen induced increase in $[Ca^{2+}]i$ and also inhibition of tyrosine phosphorylated levels of few (unexplored) proteins that involve in collagen bound GP-VI mediated intracellular signaling is worked out in this invention. (FIG. 8, 9)

The invention comprehends platelet collagen receptors GP-VI as the plausible target for the preferred compounds but put no remarks on specific receptor subtype.

The invention discloses the plasma pharmacokinetic profile of 6 over 7, the two promising compounds of the present invention; reveal good systemic availability in experimental animals correlating well with its pharmacodynamic properties. (FIG. 10)

The invention is further illustrated by the following examples which should not, however, be construed to limit the scope of the present invention.

Examples 1

Methyl 2S—N-(p-methylphenyl methyl)pyroglutamate (Compound 2)

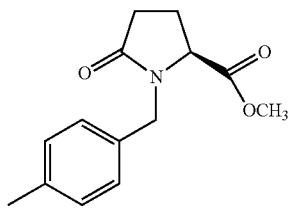

2

Methyl pyroglutamate (10 g, 1 eq, 70 mmol) was dissolved in dry THF and cooled to −30° C., fitted with a septum under $N_2$ atmosphere. LiHMDS (83.83 ml, 1.2 eq, 77 mmol) was added dropwise and stirred at this temperature for 45 min. p-methyl benzyl bromide (14.2 g, 1.1 eq, 76 mmol), dissolved in dry THF added to the reaction mixture drop wise and stirred from 0° C. to room temperature for 4 hrs. The reaction mixture was quenched with cold 1N hydrochloric acid and extracted with ethyl acetate. The organic layer was separated and dried on $Na_2SO_4$ and concentrated. The ester was purified by flash chromatography (silica gel, 230-400 mesh using chloroform as solvent system) to furnish compound 2 which was used directly in the next step.

Examples 2

Synthesis of (2S)—N-(p-methylphenyl methyl)pyroglutamic acid (Compound 3)

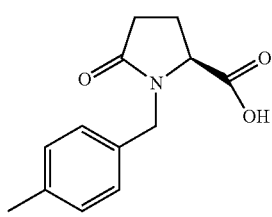

3

Compound 2 (6.0 g) was then dissolved in methanol (25 ml) and cooled to 0° C. 20% sodium carbonate solution (75 ml) was then added to the reaction mixture portion wise. The reaction mixture was then stirred at room temperature for 4 hours. Methanol was then distilled off and the reduced reaction mixture was then extracted with ether (1×25 ml). The aqueous layer was acidified with conc. HCl and extracted with ethyl acetate (3×30 ml). The organic layer was dried and concentrated to give oily product (5.2 g) which solidified on standing and was crystallized from hot ethyl acetate.

Yield: 6.9 g, 42% (crystallized product)
$[\alpha]_D^{27° C.}$: +33.96 (c=0.10; Methanol)
M.P.: 86-88° C.
IR (KBr)
3758, 3452, 2962, 1969, 1663, 1453, 1422, 1281, 1024, 801 $cm^{-1}$
$^1H$ NMR ($CDCl_3$, 200 MHz)
2.05-2.18 (m, 1H, 3-$H_a$); 2.20-2.27 (m, 1H, 3-$H_b$); 2.32 (s, 3H, —$CH_3$); 2.50-2.60 (m, 2H, 4-H); 3.88 (d, 1H, —NCHPh); 4.02-4.04 (m, 1H, 2-H); 5.09-5.17 (d, 1H, —NCHPh); 7.12 (s, 4H, Ph-H)
$^{13}C$ NMR ($CDCl_3$, 200 MHz)
14.57, 21.52, 23.26, 30.10, 45.83, 59.01, 61.00, 128.95, 129.92, 132.62, 138.11, 174.74, 176.90
FAB MS (m/z):
234 $(M+1)^+$ Example 3

Synthesis of (3R)—N-(t-butoxycarbonyl)-3-aminomethyl-piperidine (compound 4)

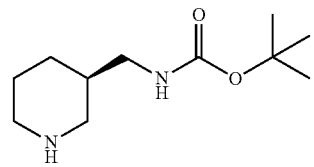

4

N-(t-butoxycarbonyl)-3-aminomethyl piperidine (10 g, 1 eq, 47 mmol), (+)-O,O'-Di-p-tolouyl-D-tartaric acid (15.52, 1 eq, 47 mmol) and dry methanol (100 ml) were mixed and heated slowly to reflux just to get a solution. This solution was cooled to room temperature and stirred at this temperature for 5-6 hours to give a white suspension of the salt which was filtered and washed with minimum quantity of dry methanol. The crude salt was crystallized once from methanol and the salt thus obtained was suspended in distilled water (25 ml) and cooled to 0° C. 10% solution of sodium carbonate solution (100 ml) was then added portion wise till the suspension was strongly basic. The reaction mixture stirred for additional 10 minutes and was extracted with ethyl acetate (5×50 ml). The combined organic layers were dried ($Na_2SO_4$) and concentrated under reduced pressure to obtain the compound of formula 4.

Yield: 3.2 g, 62%
$[\alpha]_D^{27° C.}$: −8.97 (c=1.0; Methanol)
MP: 64-66° C.
IR (Neat):
3362, 2970, 1703, 1520, 1454, 1365, 1256, 1172 $cm^{-1}$
$^1H$ NMR ($CDCl_3$, 300 MHz)
δ 1.00-1.22 (m, 2H, H-4); 1.40 (s, 9H, —O—$C(CH_3)_3$); 1.57-1.72 (m, 3H, H-3, H-5); 2.21-2.32 (m, 1H, $CH_a$NHBoc); 2.44-2.2.57 (m, 1H, $CH_b$NHBoc); 2.92-3.05 (m, 4H, H-2, H-4); 4.72 (brs, 1H, NH)
$^{13}C$ NMR ($CDCl_3$, 300 MHz)
26.56, 29.03, 29.58, 38.44, 44.99, 47.46, 51.16, 79.73, 156.72
FAB MS (m/z):
215 $[M+1]^+$, 114

Example 4

Synthesis of (3S)—N-(t-butoxycarbonyl)-3-aminomethyl-piperidine (compound 5)

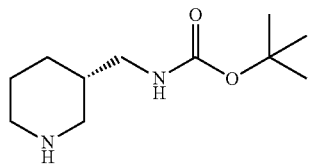

5

N-(t-butoxycarbonyl)-3-aminomethyl piperidine (10 g, 1 eq, 47 mmol), (−)-O, O'-Di-p-tolouyl-L-tartaric acid (15.52, 1 eq, 47 mmol) and dry methanol (100 ml) were mixed and heated slowly to refluxing to just to get a uniform solution. The reaction mixture was cooled to room temperature and stirred at this temperature for 5-6 hours. White solid formed was filtered out and washed with minimum quantity of dry methanol. The crude solid was recrystallized from methanol. The compound was suspended in distilled water (25 ml) and cooed to 0° C. 10% solution of sodium carbonate solution (100 ml) was then added portion wise, until basic, with stirring for 10 min. The reaction mixture was extracted with ethyl acetate (5×50 ml). The organic layer was separated, dried and concentrated under reduced pressure to obtain the compound of formula 3.

Yield: 3.28 g, 65%
$[\alpha]_D^{27°\ C.}$: +11.03 (c=0.10; Methanol)
MP: 64-66° C.
IR (Neat):
3360, 2972, 1703, 1519, 1455, 1365, 1255, 1172 cm$^{-1}$
$^1$H NMR (CDCl$_3$, 300 MHz) δ 1.01-1.21 (m, 2H, H-4); 1.39 (s, 9H, —O—C(CH$_3$)$_3$); 1.57-1.72 (m, 3H, H-3, H-5); 2.20-2.31 (m, 1H, CH$_a$NHBoc); 2.49-2.56 (m, 1H, CH$_b$NHBoc); 2.90-3.03 (m, 4H, H-2, H-4); 4.77 (brs, 1H, NH)
$^{13}$C NMR (CDCl$_3$, 300 MHz)
26.56, 29.03, 29.58, 38.44, 44.99, 47.46, 51.16, 79.73, 156.72
FAB MS (m/z):
215 (M+1)$^+$, 114

Example 5

Synthesis of (2S)-1-(4-methylphenylmethyl)-5-oxo-(3S)—{N-[(3-t-butoxycarbonyl aminomethyl)]-piperidin-1-yl}-pyrrolidine-2-carboxamide, (compound 6)

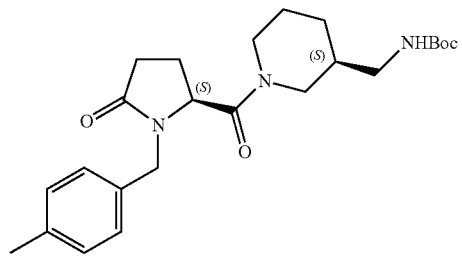

Method A

Step-1: (2S)—N-(4-methylphenylmethyl)-pyroglutamic acid, Compound 3 (3.50 g, 1 eq, 15 mmol) was dissolved in dry DCM (50 ml) and cooled to 0° C. Oxalyl chloride (1.3 ml, 1.2 eq, 18 mmol) was then added drop wise at 0° C. and the mixture was allowed to warm up to room temperature and stirred for 12 hours. The reaction mixture was then concentrated over reduced pressure.

Step-2: Compound 4 (3.53 g, 1.1 eq., 16 mmol) was dissolved in dry DCM (50 ml) and cooled to 0° C. Triethylamine (4.82 ml, 2.3 eq, 35 mmol) was then added to the reaction mixture and stirred for 10 min. The acid chloride (from step-1) dissolved in dry DCM (25 ml) was then added drop wise at 0° C. and stirred at room temperature for 3 hrs. The reaction mixture was then washed with saturated sodium bicarbonate (1×50 ml), ice cold 1N HCl (1×50 ml) and then with brine. The organic layer was separated, dried and concentrated. The viscous oil obtained was then flash chromatographed [silica gel, 230-400 mesh using chloroform-methanol (9.5:0.5) as solvent system] to get pure compound. The compound was further purified by re-crystallization from ethyl acetate-hexane.

Yield: 4.25 g, 66% (double crystallized)
$[\alpha]_D^{27°\ C.}$: +35.00 (c=0.098; Chloroform)
MP: 138-140° C.
IR (KBr):
3274, 2977, 2934, 2860, 1714, 1674, 1630, 1541, 1449, 1365, 1272, 12489, 1176, 1144, 1039, 997, 958, 847, 759, 717, 654
$^1$H NMR (CDCl$_3$; 600 MHz):
δ 1.119-1.390 (m, 2H, 4'-H); 1.448 (s, 9H, —O—C(CH$_3$)$_3$); 1.704 (m, 1H, 3'-H); 1.725-1.887 (m, 2H, 5'-H); 2.138-2.175 (m, 1H, 3-H$_a$); 2.305 (s, 3H, Ph-CH3), 2.361-2.398 (m, 1H, 3-H$_b$); 2.496-2.555 (m, 2H, 4-H); 2.646-2.757 (m, 2H, —CH$_2$—NH-Boc); 2.833-3.090 (m, 2H, 6'-H); 3.324-3.428 (m, 1H, 2'-H$_a$); 3.731-3.769 (m, 1H, 2'-H$_b$); 4.110-4.200 (m, 2H, —CH$_2$-Ph & 2-H); 4.871 (s, 1H. NH); 5.133-5.138 (d, 1H, —CH$_2$-Ph); 7.060-7.090 (dd, 4H, Ph-H)
$^{13}$C NMR (CDCl$_3$; 600 MHz):
21.063, 21.086, 22.651, 24.614, 27.898, 28.287, 28.639, 29.748, 35.955, 38.330, 42.728, 43.118, 43.332, 45.065, 45.646, 49.273, 55.673, 55.841, 79.331, 128.427, 128, 733, 129.351, 133.078, 137.339, 156.028, 168.810, 169.253, 175.164
FAB MS
(m/z): 429 (M$^+$), 330, 374, 452 (M+Na)$^+$ Method-B (2S)—N-(4-methylphenylmethyl)-pyroglutamic acid, Compound 3 (3.50 g, 1 eq, 15 mmol) and 1-hydroxy benzotrizole (3.04 g, 1.5 eq, 22.5 mmol) were dissolved in dry DCM (50 ml) in a three necked round bottom flask fitted with N$_2$ inlet. The reaction mixture was cooled to 0° C. in an ice-salt bath. Dicyclohexylcarbodiimide (DCC) (3.72 g, 1.2 eq, 18 mmol) dissolved in dry DCM (20 ml) was added to it and stirred while being at 0° C. for 15 min. (3R)—N-(t-butoxycarbonyl)-3-aminomethyl-piperidine, Compound 4 (3.21 g, 1 eq, 15 mmol) dissolved in dry DCM (20 ml) was added drop wise to the reaction mixture and stirring was continued for 3 hrs at 0° C. The reaction mixture was the brought to room temperature and concentrated under reduced pressure. The residue was dissolved in ethyl acetate, cooled to 5° C., filtered and the filtrate was washed successively with dil. citric acid (3×50 ml), dil. sodium bicarbonate solution (3×50 ml) and brine (1×50 ml). The organic layer was separated, dried and concentrated under reduced pressure. The crude material was flash chromatographed [silica gel, 230-400 mesh using chloroform-methanol (9.5:0.5) as solvent system] to get pure Compound 6, 4.5 g, 70% yield.

Method-C (2S)—N-(4-methylphenylmethyl)-pyroglutamic acid, Compound 3 (3.5 g, 1 eq, 15 mmol), (3R)—N-(t-butoxycarbonyl)-3-aminomethyl-piperidine Compound 4 (3.21 g, 1 eq, 15 mmol) and diisopropyl ethyl amine (5.36 ml, 2 eq, 30 mmol) were dissolved in dry DCM (50 ml) in a three necked round bottom flask fitted with $N_2$ inlet and rubber septa. The reaction mixture was cooled to 0° C. in an ice-salt bath and stirred for 10 min. A solution of benzotriazole-1-yl-oxy-tris-pyrrolidino-phosphonium hexafluorophosphate (7.82 g, 1 eq, 15 mmol) dissolved in dry DCM (20 ml) was added drop wise to the reaction mixture and stirring was continued for 3 hours at 0° C. The reaction mixture was then brought to room temperature and concentrated under reduced pressure. The residue was dissolved in ethyl acetate, washed successively with dil. citric acid (3×50 ml), dil. sodium bicarbonate solution (3×50 ml) and brine (1×50 ml). The organic layer was separated, dried and concentrated under reduced pressure. The crude material was flash chromatographed [silica gel, 230-400 mesh using chloroform-methanol (9.5: 0.5) as solvent system] to get pure compound 4.6 g, 72% yield.

Method-D (2S)—N-(4-methylphenylmethyl)-pyroglutamic acid Compound 3 (3.5 gm, 1 eq, 15 mmol) and dry triethyl amine (4.10 ml, 2 eq, 30 mmol) were dissolved in dry THF (50 ml) in a three necked round bottom flask fitted with dry $N_2$ inlet and rubber septa. The reaction mixture was cooled to −20° C. and stirred while being at −20° C. for 10 minutes. Isobutyl chloroformate (1.96 ml, 1 eq, 15 mmol) was added drop wise to it at −20° C. and the stirring was continued for 15 minutes. Solution of (3R)—N-(t-butoxycarbonyl)-3-aminomethyl-piperidine, Compound 4 (3.21 gm, 1 eq, 15 mmol) in dry dichloromethane (25 ml) was added drop wise to it in 10 minutes at −20° C. The reaction mixture was stirred for 1 hr at 0° C. to 25° C., quenched by adding saturated $NH_4Cl$ solution and concentrated under reduced pressure. The residue was dissolved in ethyl acetate and washed successively with dil. citric acid (3×50 ml), dil sodium bicarbonate solution (3×50 ml) and brine (1×50 ml). The organic layer was separated, dried over $Na_2SO_4$ and concentrated under reduced pressure. The crude material was flash chromatographed [silica gel, 230-400 mesh using chloroform-methanol (9.5:0.5) as solvent system] to get pure Compound 6 4.2 g, 65% yield.

Example-6

Synthesis of (2S)-1-(4-methylphenylmethyl)-5-oxo-(3R)—{N-[(3-t-butoxycarbonyl-aminomethyl)]-piperidin-1-yl}-pyrrolidine-2-carboxamide (compound 7)

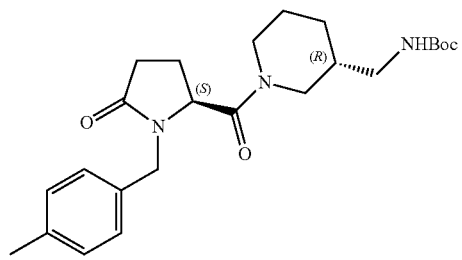

Method A

Step-1: (2S)—N-(4-methylphenylmethyl)-pyroglutamic acid, (3.50 g, 1 eq, 15 mmol) was dissolved in dry DCM (10 ml) and cooled to 0° C. Oxalyl chloride (1.3 ml, 1.2 eq, 18 mmol) was then added drop wise at 0° C. and the mixture was allowed to warm up to room temperature and stirred for 12 hours. The reaction mixture was then concentrated over reduced pressure.

Step-2: Compound 5 (3.53 g, 1.1 eq., 16 mmol) was dissolved in dry DCM (20 ml) and cooled to 0° C. Triethylamine (4.82 ml, 2.3 eq., 35 mmol) was then added to the reaction mixture and stirred for 10 min. The acid chloride (from step-1) dissolved in dry DCM (10 ml) was then added drop wise at 0° C. and stirred at room temperature for 3 hrs. The reaction mixture was then washed with saturated sodium bicarbonate (1×50 ml), ice cold 1N HCl (1×50 ml) and then with brine. The organic layer was separated, dried and concentrated. The viscous oil obtained was then flash chromatographed [silica gel, 230-400 mesh using chloroform-methanol (9.5:0.5) as solvent system] to give the compound which was further purified by re-crystallization from ethyl acetate-hexane to give pure compound, 4.38 g, 68% yield (double crystallized)

$[\alpha]_D^{27° C.}$: +5.69 (c=0.99; Chloroform)

MP: 180-182° C.

IR (KBr):

3330, 2974, 2935, 2857, 1710, 1677, 1642, 1528, 1444, 1363, 1274, 1173, 1146, 1080, 997, 958, 850, 756, 645

$^1$H NMR (CDCl$_3$; 600 MHz):

δ 1.177-1.270 (m, 2H, 4'-H); 1.424 (s, 9H, —O—C(CH$_3$)$_3$); 1.668 (m, 1H, 3'-H); 1.768-1.856 (m, 2H, 5'-H); 2.138-2.175 (m, 1H, 3-H$_a$); 2.305 (s, 3H, Ph-CH$_3$), 2.361-2.398 (m, 1H, 3-H$_b$); 2.496-2.555 (m, 2H, 4-H); 2.646-2.757 (m, 2H, —CH$_2$—NH-Boc); 2.833-2.984 (m, 2H, 6'-H); 3.324-3.428 (dd, 1H, 2'-H$_a$); 3.731-3.769 (m, 1H, 2'-H$_b$); 4.160-4.180 (m, 2H, —CH$_2$-Ph & 2-H); 4.871 (s, 1H. NH); 5.133-5.138 (m, 1H, —CH$_2$-Ph); 7.060-7.090 (dd, 4H, Ph-H);

$^{13}$C NMR (CDCl$_3$; 600 MHz):

21.086, 22.728, 23.866, 24.614, 28.096, 28.303, 28.700, 29.784, 36.405, 37.322, 42.828, 43.011, 43.263, 45.042, 45.852, 48.441, 55.986, 56.047, 79.316, 128.389, 128.710, 129.336, 133.048, 137.339, 156.080, 168.810, 169.001, 175.072

FAB MS (m/z): 429 (M$^+$), 330, 374, 452 (M+Na)$^+$

Biological Study

In Vitro Studies

From human subjects blood was collected in citrate-phosphate-dextrose (CPD) (1:7) from healthy volunteers (age between 18-60 years) after prior consent. A detailed medical history and physical examination was carried out before phlebotomy. The donors were free from heart, lung, kidney disease, cancer, epilepsy, diabetes, tuberculosis, abnormal bleeding tendency, allergic disease, sexually transmitted diseases, jaundice, malaria, typhoid and thyroid or any other endocrine disorder. Donors were free from any prior medication for last 72 hours.

Preparation of Washed Platelets

Fresh blood was drawn by venipuncture from consenting healthy human volunteers in citrate-phosphate-dextrose. Platelet-rich plasma (PRP) was obtained by centrifugation at 180 g for 20 minutes at room temperature (Beckman T J6, USA). 10% (v/v) of ACD buffer (39 mM citric acid, 75 mM tri-sodium citrate.2H$_2$O, 135 mM D-glucose, pH 4.5) was added, and the platelet-rich plasma was spun at 800 g for 10 minutes (3K30 Sigma Centrifuge, Germany). Platelets were then washed twice with Buffer (20 mM HEPES, 138 mM NaCl, 2.9 mM KCl, 1 mM MgCl$_2$, 0.36 mM NaH$_2$PO$_4$, 1 mM EGTA, 4.77 mM trisodium citrate, and 2.35 mM citric acid, 5 mM glucose and Apyrase 1 U/ml, pH 6.5) containing 0.1% bovine serum albumin (BSA) and finally resuspended in the HEPES-buffered Tyrode solution (pH 7.4), to give a concentration of 2×10⁸ cells/mL (Jandrot-Perrus M, Lagrue A H, Okuma M, and Boni C *Adhesion and Activation of Human Platelets Induced by Convulxin Involve Glycoprotein VI and Integrin α2β1 J. Biol. Chem.* 1997; 272: 27035-27041).

Platelet Aggregation Measurements

A turbidimetric method was applied to measure platelet aggregation, using a Dual channel-Aggregometer (560 Ca, 230 VAC Chronolog-corp, Havertown, USA (Dikshit M, Kumari R, Srimal R C. *Pulmonary thromboembolism induced alterations in nitric oxide release from rat circulating neutrophils. The Journal of Pharmacology and Experimental Therapeutics* 1993; 265:1369-1373). Platelet rich plasma (1×10⁸ platelets/ml, 0.45 ml) was pre-warmed to 37° C. for 2 min, then incubated with compound (3-100 μM) or an isovolumetric solvent control (0.5% DMSO) for 5 min before addition of the agonists (i.e., 2 μg/ml Collagen, 10 μM ADP, 1 U/ml Thrombin, 15 ng/ml Convulxin, 25 μM TRAP, 1.5 mg/ml Ristocetin). The reaction was allowed to proceed for at least 5 min, and the extent of aggregation was expressed in light-transmission units (Ivandic B T, Schlick P, Staritz P, Kurz K, Katas H A, Giannitsis E. *Determination of clopidogrel resistance by whole blood platelet aggregometry and inhibitors of the P2Y12 receptor. Clinical Chemistry* 2006; 52:383-88).

The percentage of aggregation was calculated by using following formula:

$$\text{Percent Aggregation} = A/B \times 100$$

Where, A is the number of division traversed by the label on chart in the presence of Inducer & B is the total number of divisions (80).

Figure 3:
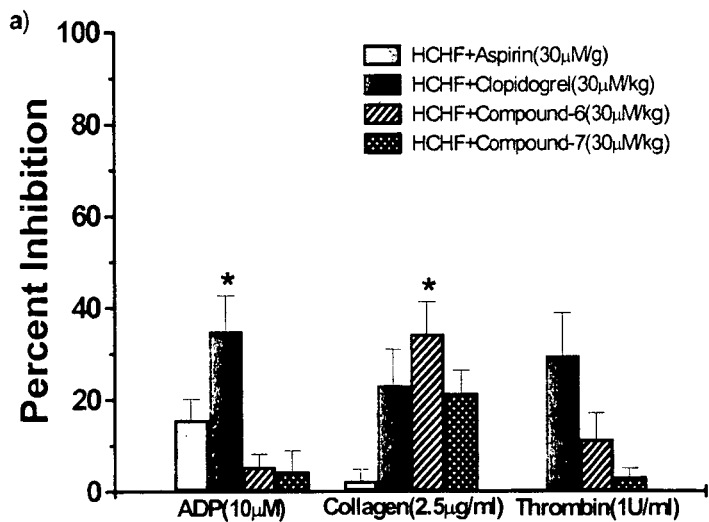

Platelet Aggregation Studies (FIG. 3)

a) Platelet Aggregation (Human, In Vitro) (FIG. 3*a* (i) (ii) (iii))

The invention including compound 1, compound 6 & 7 were found to be active against collagen induced aggregation in vitro in human platelet rich plasma.

The in vitro anti-aggregatory activity was comparable among all the three compounds as they inhibited collagen mediated effects at similar concentrations.

The invention Compound 6 and 7 did not exhibit any effect on ADP and thrombin mimetic up to 300 μM, SFLLRN (TRAP) induced platelet aggregation, while Compound 1 exhibited a significant inhibition against TRAP induced platelet aggregation even at 100 μM, thereby displaying its non-specific mode of action.

The compounds had no inhibitory effect against platelet aggregation induced by another GP VI agonist, Convulxin and GP 1b specific agonist, Ristocetin.

Inference form FIG. 3*a* could be drawn as that the compound 1, 6 and 7 are active against collagen induced aggregation in vitro in human platelet rich plasma while no effect on ADP induced platelet aggregation. Moreover the compound 6 and 7 are more specific than compound 1 which exhibits moderate efficacy against thrombin mimetic, SFLLRN (TRAP) induced platelet aggregation. The invention further had no inhibitory effect on platelet aggregation induced by GP VI specific agonist Convulxin and GP 1b specific agonist, Ristocetin.

Platelet Aggregation (Mice, Ex Vivo) (FIG. 3 *b*)

The compound 6 exhibits dose dependent inhibition in platelet aggregation (ex vivo) induced by collagen when administered to mice via oral route Inference could be that the compound 6 specifically inhibits collagen induced platelet aggregation.

GPVI- and α2β1-Mediated Platelet Adhesion Assay

Integrin α2β1 binding on soluble collagen depends on the presence of Mg²⁺/Ca²⁺ (Onley D. J., Knight C. G., Tuckwell D. S., Barnes M. J., and Farndale R. W. *Micromolar Ca2+ concentrations are essential for Mg2+-dependent binding of collagen by the integrin α2β1 in human platelets. J. Biol. Chem.* 2000; 275: 24560-24564.) while GPVI mediates adhesion over fibrillar collagen in absence of divalent ions (Nieswandt B., Brakebusch C, Bergmeier W, Schulte V, Bouvard D, Nejad R M, Lindhout T., Heemskerk J W M, Zirngibl H and Fassler R. *Glycoprotein VI but not α2β1 integrin is essential for platelet interaction with collagen. The EMBO Journal,* 2001; 20:2120-2130) and therefore the adhesion assays were performed in the presence or absence of these divalent cations. Ninety-six well micro titer plates were coated with insoluble equine tendon fibrillar type I collagen or soluble rat tail type I (non-fibrillar) collagen, maintained in acetate buffer (pH 4.5), (Nakamura T., Jamieson G. A., Okuma M., Kambayashi J., and Tandon N. N. *Platelet Adhesion to Native Type I Collagen Fibrils: role of gpVI in divalent cation-dependent and-independent adhesion and thromboxane A2 generation. J. Biol. Chem.* 1998; 273: 4338-4334, Tandon N N, Ockenhouse C F, Greco N J, Jamieson G A. *Adhesive functions of platelet lacking GPIV (CD36). Blood* 1991; 78: 2809-13). The unoccupied protein binding sites on the wells were blocked with 5 mg/ml BSA at room temperature for 1 hour, and then rinsed once in PBS. Washed platelets, suspended in the Tyrode's-HEPES buffer (136.7 mM NaCl, 13.8 mM NaHCO₃, 0.36 mM NaH₂PO₄.H₂O, 2.6 mM KCl, 1.0 mM MgCl₂.6H₂O, 5.5 mM glucose, 0.5% BSA, pH 7.4) at 1×10⁸ cells/mL were pre-incubated with compounds for 30 min at 37° C. and added to the wells (10⁷/well) for 1 h at room temperature. Divalent cation-free adhesion buffer was made by replacing Mg²⁺ (1 mM) in the Tyrode-HEPES buffer with 50 μM EDTA (Yoshida S., Sudo T., Niimi M., Tao L., Sun B., Kambayashi J., Watanabe H., Luo E., and Matsuoka H. *Inhibition of collagen-induced platelet aggregation by anopheline antiplatelet protein, a saliva protein from a malaria vector mosquito. Blood* 2007; 111: 2007-201). After three washes in Tyrode's buffer, the number of adherent platelets was evaluated colorimetrically (as described by Bellavite P., Andrioli G., Gizzo P., Arigliano P., Chirumbolo S., Manzato F., Santonastaso C. *A colorimetric method for the measurement of platelet adhesion in microtiter plates. Anal. Biochem.* 1994; 216:444-450. Briefly, 150 μl of a 0.1 M citrate buffer (pH 5.4), containing 5 mM p-nitrophenyl phosphate and 0.1% TritonX-100 was added to the wells after washing. After incubation for 60 min at 25° C. in the absence of ambient light, colour was developed by the addition of 100 μl of 2N NaOH and the absorbance at 405 nm was read using a microplate reader (Powerware XS, Biotek, USA).

Platelet Adhesion Studies (FIG. 4*a*)

GPVI- and α2β1-Mediated Platelet Adhesion Assay on Collagen (Human, In-Vitro)

1) The Compounds 6 and 7 partially inhibited both fibrillar and soluble collagen mediated human platelet adhesion over collagen (in vitro) while the effect seemed to be more prominent against fibrillar collagen mediated pathway.

Inference could be drawn as that the compound 6 is better than compound 7 in inhibiting platelet adhesion over collagen coated surface.

Platelet Adhesion (Mice, Ex-Vivo) (FIG. 4 *b*)

The compound 6 exhibits dose dependent inhibition in platelet adhesion (ex vivo) over collagen surface when administered to mice via oral route.

However aspirin did not exhibit any inhibitory effect on platelet adhesion over collagen coating Inference could be drawn as that the compound 6 exhibits dose dependent reduction in platelet adhesion over collagen matrix and comparatively better than aspirin.

Measurement of Intracellular Calcium Concentration $Ca^{+2}$ concentration ($[Ca^{+2}]i$) were monitored by Fura-2AM fluorescence in the platelets (Fowler C J, Tiger G *Calibration of Fura-2 signals introduces errors into measurement of thrombin-stimulated calcium mobilization in human platelets. Clinica Chimica Acta.* 1997; 265:247-261). Human PRP was incubated with 5 µM Fura-2 AM (Sigma) for 60 minutes at 37° C. After 2 washes with the wash buffer, the platelets were resuspended at $2 \times 10^8$ cells/mL with the Tyrode's-HEPES buffer. After incubating with various concentrations of compound for 5 minutes, the platelets were stimulated with collagen (5 µg/mL) (the concentration of collagen was varied in accordance with cell number). The Fura-2 fluorescence was measured for 5 minutes at an excitation wavelength of 340/380 nm and emission wavelength of 500 nm (Yoshida S., Sudo T., Niimi M., Tao L., Sun B., Kambayashi J., Watanabe H., Luo E., and Matsuoka H. *Inhibition of collagen-induced platelet aggregation by anopheline antiplatelet protein, a saliva protein from a malaria vector mosquito. Blood* 2007; 111: 2007-201) using a fluorescence spectrophotometer (VARIAN, Cary Eclipse).

Measurement of Intracellular Calcium Concentration (FIG. 8)

Since an increase in $[Ca^{2+}]i$ is considered to play a pivotal role in platelet aggregation, the possible involvement of Compound 6 in the regulation of $[Ca^{2+}]i$ was investigated. The compound 6 exhibited a concentration dependent inhibition in enhanced calcium mobilization during collagen stimulation.

Inference could be drawn as that the compound 6 inhibited $[Ca^{2+}]i$ mobilization in a concentration dependent manner.

Immunoblotting

Platelet rich plasma ($2 \times 10^8$/ml) was pre-incubated with test compound (10-100 µM) or the isovolumetric solvent control (0.5% DMSO) for 5 minutes, followed by the addition of collagen, to trigger platelet activation. The reaction was stopped by the addition of ice cold stop buffer (5 mM EDTA, 5 mM EGTA) and the suspensions were centrifuged at 800×g for 10 minutes and then immediately resuspended in 300 µl of lysis buffer (50 mM HEPES, 5 mM EDTA, 50 mM NaCl, 1% Triton X-100, 10 µg/ml aprotinin, 1 mM PMSF, 10 µg/ml leupeptin, 10 mM NaF, 1 mM sodium orthovanadate, and 5 mM sodium pyrophosphate) (Ezumi Y, Shindoh K, Tsuji M, and Takayama H *Physical and Functional Association of the Src Family Kinases Fyn and Lyn with the Collagen Receptor Glycoprotein VI-Fc Receptorg Chain Complex on Human Platelets. J. Exp. Med.* 1998; 188: 267-276). Lysates were centrifuged at 12,000×g for 5 minutes, after which the supernatants were dissolved in Laemmeli sample buffer (Laemmeli, 1970). Samples containing 30 µg of protein were separated on 8% SDS-PAGE; the proteins were electrotransferred to a nitrocellulose membrane by semi-dry method (Amersham Biosciences). The membranes were blocked with TBST (10 mM Tris-base, 100 mM NaCl, and 0.01% Tween 20) containing 5% BSA overnight at 4° C., then probed with following primary antibodies for 2 h: anti-p-Tyr (PY20:4 G10-1:1) (diluted 1:10000 in TBST) or β-Actin (1:5000). Membranes were washed for 30 minutes and then incubated with horseradish peroxidase-linked anti-mouse IgG (diluted 1:20000 in TBST) and anti-Rabbit IgG (1:5000) for 1 h. Immunoreactive bands were detected by chemiluminescence using the ECL-enhanced chemiluminescence system (Inoue K, Ozaki Y, Satoh K, Wu Y, Yatomi Y, Shin Y and Morita T *Signal Transduction Pathways Mediated by Glycoprotein Ia/IIa in Human Platelets: Comparison with those of Glycoprotein VI. Biochem. I and Biophys. Res. Comm.* 1999; 256: 114-120).

Immunoblotting (FIG. 9)

1) The activation of platelets by collagen contributes to the assembly and stabilization of various signaling complexes. This involves tyrosine phosphorylation of various proteins in platelets.
2) The compound 6 attenuated the tyrosine phosphorylation of various proteins in collagen stimulated platelets in a concentration dependent manner.

Inference could be drawn as that the compound 6 inhibited the tyrosine phosphorylation of platelet proteins following collagen stimulation.

Amidolytic Assay of Thrombin Activity (FIG. 5)

In previous experiments, the compound 1 exhibited a significant inhibitory effect on thrombin amidolytic activity at 300 µM and 1 mM after 15 min of substrate incubation. The compound 7 actively attenuated the proteolytic cleavage of substrate by thrombin in a concentration dependent manner. The compound 6 in contrast, remained ineffective and did not exhibit any thrombin inhibitory action or concentration dependency.

Inference could drawn as that the compound 1 and 7 non-specifically attenuated thrombin amidolytic activity while compound 6 did not exhibit any of such non-specific thrombin inhibitory property.

Animal Model Studies (Ex Vivo/In Vivo Models)

The animals were obtained from the National Laboratory Animal Centre of Central Drug Research Institute, Lucknow. All the animal experiments were subjected to Institutional Animal Ethical Committee (IAEC) guidelines and were conducted according to the guidelines of Experimental Animal Care issued by the Committee for Purpose of Control and Supervision of Experiments on Animals (CPCSEA). The animals were housed in polypropylene cages and maintained on standard chow diet and water ad libitum and on 12 hr/12 hr light-dark cycle at temperature: 25±2° C., humidity: 45-55% and ventilation: 10-12 exchanges/hr.

Collagen Epinephrine Induced Pulmonary Thromboembolism:

To assess the antithrombotic efficacy of Compounds, mice were divided into vehicle, aspirin and Compounds treated groups, and each group included ten animals. Pulmonary thromboembolism was induced by injecting a mixture of collagen (150 µg/ml) and adrenaline (50 µg/ml) into the tail vein to achieve final doses of collagen (1.5 mg/kg) and adrenaline (0.5 mg/kg) to induce hind limb paralysis or death. Results have been reported as percentage protection, which represents protection against collagen and epinephrine induced thrombosis and expressed as:

$$\text{Percent Protection} = (1 - (P_{test}/P_{control})) \times 100$$

$P_{test}$—number of animals paralyzed/dead in test compound-treated group;

$P_{control}$—number of animals paralyzed/dead in vehicle treated group.

Collagen Epinephrine Induced Pulmonary Thromboembolism (FIG. 1):

a) The compound 6 (30 µM/Kg) displayed a remarkable antithrombotic efficacy (1 hr p.o dosing) which sustained for more than 24 hours and thus highlights its excellent bioavailability.

b) The compound 6 exhibited significant antithrombotic efficacy even up to 24 hours of its administration. Although the Compound 1 exhibited almost similar efficacy like compound 6, but only up to 12 hours after which it gradually becomes ineffective, while compound 7 displayed relatively weaker antithrombotic potential throughout which was maintained for up to 12 hours, after which it also declined.

c) The standard anti-platelet drugs aspirin (170 µM/kg) and clopidogrel (70 µM/kg) were effective only up to 5 hours after which their effect perishes and that too at a very high dose sufficient enough to cause bleeding complications.

Bleeding Time

Bleeding time in mice was evaluated by the method of Dejana et al, (Dejana E, Callioni A, Quintana A, Gaetano G. *Bleeding time in laboratory animals. II—A comparison of different assay conditions in rats. Thromb Res.* 1979; 15:191-7). The tail 2 mm from tip of mice was incised and the blood oozed was soaked on a filter paper, which was monitored at an interval of 10-15 sec till the bleeding stops. The time elapsed from the tip incision to the stoppage of bleeding was determined as the bleeding time. The preferred compounds, aspirin (30 mg/kg) or vehicle was given orally 60 min prior to the tail incision in a group of 5 mice each.

Bleeding Time in Mice (FIG. 2)

An ideal antithrombotic drug is expected to maintain the precarious balance between prevention of thrombosis and leaving haemostasis sufficiently intact to prevent haemorrhage.

a) Bleeding time was found to be significantly prolonged in standard anti-platelet drugs, aspirin (170 µM/kg) and clopidogrel (30 µM/kg) treated mice, at the dose most effective to prevent thrombosis.

b) The compound 1, 6 and 7 (30 µM/kg, 1 hr p.o. dosing) exhibited a mild prolongation in bleeding time (approximately 1.5 fold) which was significantly less as compared to the standard anti-platelet drug, aspirin and clopidogrel.

Inference from FIG. 2 could be drawn as that at equal efficacy, Compound 6 is comparatively safer than standard drug Aspirin and clopidogrel.

$FeCl_3$ Induced Thrombosis in Rats:

Male SD rats were anesthetized by urethane (1.25 g/kg, i.p.). The carotid artery was carefully dissected and a pulsed Doppler Probe (DBF-120A-CPx, CBI-8000, Crystal Biotech, USA) was placed around it to record the blood flow velocity and patency of the blood vessels. The carotid artery thrombosis was induced by $FeCl_3$ as follows: a square (1×1 mm) of Whatman Chromatography paper was immersed in 20% $FeCl_3$ solution for 5 min and placed on the carotid artery as described earlier (Kurz K D, Main B W, Sandusky G E. *Rat model of arterial thrombosis induced by ferric chloride. Thromb Res* 1990; 60(4):269-80). Thrombosis was monitored as the reduction in carotid artery blood flow. The time at which the blood-flow velocity was decreased to zero was recorded as the total of occlusion (TTO) of the carotid artery. When the blood flow velocity did not occlude within 120 minutes the time to thrombotic occlusion was assigned a value of >120 minutes. (Ferric Chloride Induced Thrombosis (FIG. 7))

$FeCl_3$ Induced Thrombosis in Rats (FIG. 7a):

1. The test compound 6 significantly prolonged the time to occlude the carotid artery in rats, thus displaying its remarkable antithrombotic potential, while Compound 1 failed to exhibit any protection at the same dose (FIG. 7a (i)).
2. The standard anti-platelet drug aspirin, even at a very high dose, remained ineffective in prolonging the time to occlusion in the same.
3. The COMPOUND 6 (10, 30 & 100 µMl/kg) dose dependently exhibited prolongation in time to occlusion compared to normal rats with significant elevation at 30 & 100 µM/kg in rats (FIG. 7a (ii)).

Inference could be made to the fact that the compound 1 is ineffective while compound 6 exhibits significant protection and is thus better.

Arterio-Venous Shunt Model in Rats

Rats were grouped into control, aspirin and test compound group, each group having six animals. Rats were anesthetized with urethane (1.25 g/kg). Cervical incision was made and carotid artery and its contra lateral jugular vein was exposed to prepare a shunt by using polyethylene tubes. Two 7 cm siliconized polyethylene tubes (0.5/1.0 mm inner/outer diameter) were linked to a central 6 cm silicon tube (1.0/1.5 mm, inner/outer diameter) containing a 5 cm silk thread (pre-weighed) and were filled with saline. The shunt assembly was cannulated between the jugular vein and contra-lateral carotid artery and blood was allowed to circulate through the shunt. Blood flow through the shunt was maintained for 10 minutes, subsequently the central part of the shunt was removed and silk thread having thrombus deposit was taken out and weighed. The thrombus adhered/deposited on thread was calculated by subtracting the wet weight of the silk thread. The standard drugs and test compounds were given 1 hr prior to the establishment of arterio-venous shunt (Tohti I, Tursun M, Umar A, Turdi S, Imin H, Moore N. *Aqueous extracts of Ocimum basilicum L. (sweet basil) decrease platelet aggregation induced by ADP and thrombin in vitro and rats arterio-venous shunt thrombosis in vivo. Thrombosis Res.* 2006; 118: 733-739).

Arterio-Venous Shunt Model in Rats (FIG. 6a)

The compound 6 and 7 were almost equally effective in reducing the thrombus weight significantly and their efficacy was comparable to those of standard anti-platelet drugs, aspirin and clopidogrel in rats.

The inference could be made as that the antithrombotic efficacy of both compound 6 and 7 is identical.

Hyperlipidemic Hamster Model

Golden Syrian hamster (100-120 g) obtained from the National Laboratory Animal Centre of Central Drug Research Institute, Lucknow was used in this study. All the procedures involving hamsters were subject to Institutional Animal Ethical Committee (IAEC) guidelines. The animals were housed in polypropylene cages and maintained on standard chow diet and water ad libitum and on 12 hr/12 hr light-dark cycle at temperature 25±2° C., humidity 45-55% and ventilation: 10-12 exchange/hr. Animals were randomly divided into one of two groups, Normal chow fed (Protein 186.2 g/kg, fat 62.5 g/kg, fibre 45.3 g/kg, Nitrogen free extract 537.7 g/kg, Vitamins, Minerals), and HCHF fed (Chow diet supplemented with 3% Cholesterol and 15% Saturated fat) for three months (n=16). These groups were again divided into those receiving aspirin (30 µM) or vehicle (in gum acacia suspension) or one of the preferred compounds (Example-1 or Example-15) (30 µM/Kg). After the twelve-week feeding period, the animals were fasted for 14 hours prior to sacrifice (Cheema S K, Cornish M L., *Bio F1B hamster: a unique animal model with reduced lipoprotein lipase activity to investigate nutrient mediated regulation of lipoprotein metabolism. Nutrition & Metabolism* 2007, 4:27). The hamsters were anaesthetized by anesthetic ether sniffing, heart was punctured and fasting blood samples were collected in tubes containing 2.5% tri sodium citrate. Some amount of Whole blood was used for aggregation studies and remaining whole blood was centrifuged at 180 g for ten minutes for separation of platelet rich plasma (PRP). 10% ACD (39 mM citric acid, 75 mM tri-sodium citrate, 135 mM D-glucose, pH 4.5) was added to Platelet rich plasma and was spun at 800 g for 10 min to get platelet pellet and platelet poor plasma (PPP). Platelet poor plasma was used for coagulation studies and while platelets were used to assess adhesion over collagen coated surface.

Platelet Adhesion on Collagen Coated Surface (Hyperlipidemic Hamsters)

Platelet adhesion to collagen was measured in polystyrene 96-well micro titer plates. Micro titer plates were coated with insoluble equine tendon native fibrillar type I collagen (Chrono-Log Corp. Havertown, USA), 2 µg/well in 5 mM acetic acid (Tandon N N, Ockenhouse C F, Greco N J, Jamieson G A. *Adhesive functions of platelet lacking GPIV (CD36). Blood* 1991; 78: 2809-13) overnight at 4° C. The unoccupied protein binding sites on the wells were blocked with 0.5% BSA in Tyrode's-HEPES buffer (136.7 mM NaCl, 13.8 mM $NaHCO_3$, 0.36 mM $NaH_2PO_4.H_2O$, 2.6 mM KCl, 1.0 mM $MgCl_2.6H_2O$, 5.5 mM glucose, pH 7.4) at room temperature for 1 hour, and then rinsed once with PBS. Washed platelets were suspended in the Tyrode's-HEPES buffer and added to the wells ($2 \times 10^7$ cells/well) for 1 h at room temperature. After three washes with PBS, the number of adherent platelets was evaluated colorimetrically (Bellavite P., Andrioli G., Gizzo P., Arigliano P., Chirumbolo S., Manzato F., Santonastaso C. *A colorimetric method for the measurement of platelet adhesion in microtiter plates. Anal. Biochem.* 1994; 216:444-450). Briefly, 150 µl of a 0.1 M citrate buffer (pH 5.4), containing 5 mM p-nitrophenyl phosphate and 0.1% TritonX-100 was added to the wells after washing. After incubation for 30 minutes at 25° C. in the absence of ambient light, colour was developed by the addition of 100 µl of 2N NaOH and the absorbance at 405 nm was read using a microplate reader (Powerware XS, Biotek, USA).

Platelet Adhesion on Collagen Coated Surface (Hyperlipidemic Hamster Model, Ex-Vivo) (FIG. 4 c)
1) The standard anti-platelet drug aspirin displayed no alteration in platelet adhesion while clopidogrel exhibited a significant reduction in platelet adhesion over collagen coated surface.
2) The compound 6 but not 7 exhibited a significant inhibition in platelet adhesion over collagen surface in hyperlipidemic hamster model of atherosclerosis, with a better efficacy profile than aspirin.
3) Further the compound 6 exhibited a dose dependent inhibition in platelet adhesion over collagen coated surface.

The inference could be drawn as that the compound 6 exhibits significant attenuation in platelet adhesion over collagen surface in contrast to compound 7 which exhibits no effect on the same.

Whole Blood Aggregation

Whole blood aggregation studies were performed on a dual channel aggregometer (560 Ca, 230 VAC, Chrono-log Corp, USA) using the impedance method (Ivandic et al, 2006). The citrated whole blood (450 µl) were mixed by gentle inversion then diluted with physiological saline (0.9% NaCl, 450 µl) and calcium chloride (10 µl, 1.0% w/v), were incubated at (37° C.) until the time of use. Aggregation response was taken after adding inducers at the following final concentrations: ADP 10 µM; Thrombin 1 U/ml, Collagen 2.5 µg/ml, with stirring. After inducers addition, the impedance was measured over a time interval of 6 minutes. Platelet aggregation was measured by calculating impedance (Ohms). The percentage of aggregation was calculated by conventional method as described earlier (Torres Duarte A P, Dong Q S, Young J, Abi-Younes S, Myers A K. *Inhibition of platelet aggregation in whole blood by alcohol. Thromb Res* 1995; 78 (2):107-15, Kumari R, Singh M P, Seth P, Dikshit M. *Inhibition of platelet aggregation by a protein factor present in rat peripheral polymorphonuclear leukocyte supernatant. Thromb Res* 1998; 91 (2):75-82).

Whole Blood Aggregation in Hyperlipidemic Hamsters (Ex Vivo) (FIG. 3c)
1) The mean maximal platelet aggregation in response to ADP, collagen and thrombin was found to be significantly increased in high cholesterol high fat diet fed hamsters compared with those on normal chow.
2) Aspirin (100 µM/kg) treated HCHF hamsters displayed reduced platelet aggregation in response to collagen but not in ADP and thrombin mediated effects.
3) Clopidogrel (30 µM/kg) treatment also inhibited ADP and collagen induced platelet aggregation but not thrombin mediated platelet responses.
4) The invention (Example-6) significantly inhibited collagen induced platelet Aggregation in high fat group in dose dependent manner while example 7 was unable to do so. Also ADP and thrombin induced activation remained unhindered.

Inference could be drawn as that the Compound 6 is better than Compound 7 in attenuating collagen stimulated platelet aggregation in hyperlipidemic hamsters.

$FeCl_3$ Induced Thrombosis in Hyperlipidemic Hamsters

HCHF treated hamsters were anesthetized by urethane (1.25 g/kg, i.p.). The carotid artery was carefully dissected and a pulsed Doppler Probe (DBF-120A-CPx, CBI-8000, Crystal Biotech, USA) was placed around it to record the blood flow velocity and potency of the blood vessels. The carotid artery thrombosis was induced by $FeCl_3$ as follows: a square (1×1 mm) of Whatman Chromatography paper was immersed in 30% $FeCl_3$ solution for 5 min and placed on the carotid artery as described earlier (Kurz K D, Main B W, Sandusky G E. *Rat model of arterial thrombosis induced by ferric chloride. Thromb Res* 1990; 60(4):269-80). Thrombosis was monitored as the reduction in carotid artery blood flow. The time at which the blood-flow velocity was decreased to zero was recorded as the total of occlusion of the vessel.

b) $FeCl_3$ Induced Thrombosis in Hyperlipidemic Hamsters (FIG. 7b):
1) High fat diet treatment reduced the time to occlude the carotid artery, thus displaying the incidence of a pro-thrombotic state during hyperlipidemia in hamsters.
2) The standard antithrombotic drugs aspirin and clopidogrel significantly prolonged the time to occlusion (TTO) in hamsters.
3) The compound 6 significantly increased the time to occlusion in hamsters, thus confirming its substantial antithrombotic efficacy in a disease model, while compound 1 and compound 7 remained ineffective and thus did not display antithrombotic characteristic in the same.

Inference could be made to the fact that the compound 1 and 7 were ineffective while compound 6 significantly prolonged the time to occlusion and is therefore better than the two.

Arterio-Venous Shunt Model in Hyperlipidemic Hamsters (FIG. 6b):
1) High fat diet treatment significantly increased the thrombus weight, thus displaying a pro-thrombotic state induced by hyperlipidemic diet mimicking the clinical condition.
2) The standard antithrombotic drugs aspirin and clopidogrel significantly reduced the weight of thrombus formed.
3) The Compound 6 significantly reduced the thrombus weight even at a very low dose (10 µM/kg) and was almost equivalent to those of standard drugs.
4) The inference could be made as that the compound 6 significantly reduces thrombus weight even at 10 µM/kg and is better.

Pharmaco-Kinetic Data (FIG. 10)

In-vivo pharmacokinetic parameters were generated in male NZ rabbits at a dose of 20 mg/kg by oral route of administration. The blood samples were drawn at 0.25 0.5, 0.75, 1, 1.5, 2, 4, 6, 8, 10, 12, 18 and 24 hr post dose, processed and analyzed by Liquid Chromatography-Mass Spectrometry (LC-MS). Plasma concentration at different time points were plotted to give Plasma Concentration Time Profile and the data was fitted non-compartmentally using Win NonLin 5.1 version software and the estimates of pharmacokinetic parameters were derived with SD mean values. Maximum plasma concentration ($C_{max}$), time to achieve maximum plasma concentration ($t_{max}$), Area under curve (AUC) and mean residence time (MRT) of Compound 1, Compound 6 and Compound 7 are given in Table-1.

TABLE 1 represents estimates of pharmacokinetic parameters of 6 and 7 in male NZ rabbits at a dose of 20 mg/kg body weight

| PK Parameters | Compound 1(a) 1:1 Mixture of 6 & 7 | Compound 6 | Compound 7 |
|---|---|---|---|
| Cmax (ng/ml) | 947.02 ± 237.4 | 149.49 ± 53.12 | 112.40 ± 10.25 |
| Tmax (h) | 0.68 ± 0.29 | 0.75 ± 0.144 | 8.67 ± 0.66 |
| AUC (ng · h/ml) | 6524.15 ± 1502.7 | 874.8 ± 232.01 | 1112.81 ± 169.77 |
| MRT (h) | 16.20 ± 1.46 | 5.25 ± 1.75 | 16.20 ± 1.46 |

Summary of the Biological Assays

TABLE 2

Summary of the biological assays

| Test systems | 1:1 mixture of 6 & 7 | Compound 6 | Compound 7 | Inference |
|---|---|---|---|---|
| Collagen-epinephrine induced thrombosis in mice | Up to 18 hrs | >24 hrs | <12 hrs | Compound 6 more active, Effect is long lasting |
| Bleeding Time in mice | 2 fold | 1.5 fold | 1.5 fold | At equal efficacy Compound 6 is more safe |
| Arterio-venous shunt model in rat | Protective | Protective | Protective | Similar activity |
| Arterio-venous shunt model in hyper-lipidemic hamsters | | Protective Even at 10 μM | | Compound 6 is better |
| Ferric chloride induced thrombosis in rats | Not protective | Protective | | Compound 6 is better |
| Ferric chloride induced thrombosis in hyper-lipidemic hamsters | Not protective | Protective | Not protective | Compound 6 is better |
| Collagen induced platelet aggregation studies (Human) IC50 | ~10 μM | ~10 μM | >10 μM | Compound 6 is better than Compound 7 |
| TRAP induced platelet aggregation studies (Human) IC50 | >100 μM | >500 μM | >500 μM | Both compound 6 & 7 are more specific than the mixture |
| Platelet adhesion | Effective (100 μM) | Effective (30 &100 μM) | Effective (100 μM) | Compound 6 is better |
| Whole blood aggregation in hyperlipidemic hamsters | Effective | Effective | No effect | Compound 6 is better than Compound 7 |
| Platelet adhesion hyperlipidemic hamsters | Effective | Effective | No effect | Compound 6 is better than Compound 7 |

Advantages:

1. The compounds of the present invention act as inhibitors of collagen induced platelet activation and adhesion
2. The other advantage is to avoid any racemization at the α-carboxylic center, during N-alkylation, the reagent LiHMDS at low temperatures is claimed to furnish Methyl N-p-methyl-phenylmethyl]pyroglutamate in good chiral purity.
3. Further advantage is to avoid any racemization at the α-carboxylic center.
4. The compounds of the present invention showed fast absorption with effective $C_{max}$ values
5. The compounds of the present invention showed optimum levels of solubility
6. The compounds of the present invention showed low plasma levels
7. The compounds of the present invention showed low peripheral accumulation
8. The compounds of the present invention showed lower levels of toxicity

We claim:

1. Isolated diastereomer compound of formula 6 or 7 having general formula 1-(4-methylphenylmethyl)-5-oxo-{N-[(3-t-butoxycarbonyl-aminomethyl)]-piperidin-1-yl}-pyrrolidine-2-carboxamides;

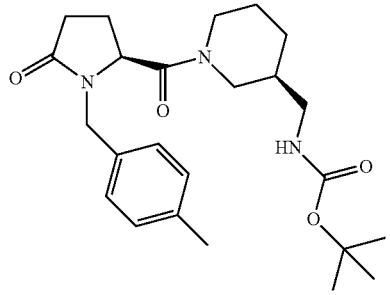
6

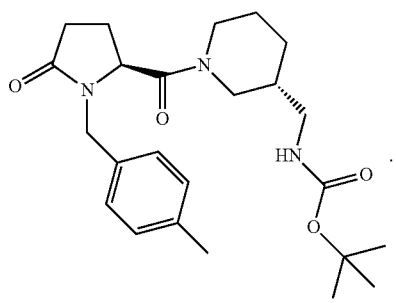
7

2. A process for the a preparation of compound of formula 6 and a compound of formula 7

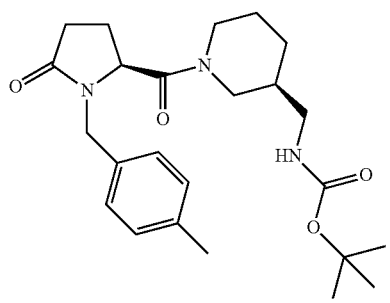
6

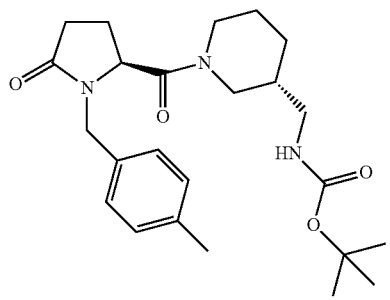
7 wherein the process comprises the steps of:
a) reacting methyl pyroglutamate with p-methyl benzyl bromide in an aprotic solvent in presence of LiHMDS at a temperature ranging between 0 to 350 C for a period ranging between 1 to 4 hr, quenching the reaction mixture with HCl and obtaining the compound of formula 2

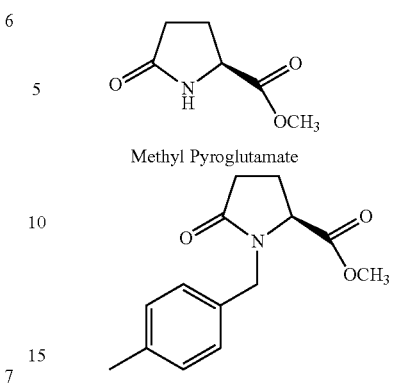
formula 2

Methyl Pyroglutamate b) reacting compound of formula 2 with sodium carbonate at a temperature ranging between 0° C. to 30° C. for a period ranging between 0.5 to 4 hr to obtain 2S)—N-(p-methylphenylmethyl) pyroglutamic acid of formula 3;

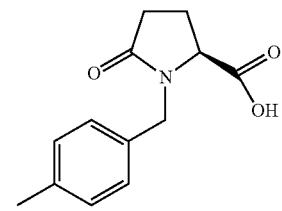
formula 3 c) reacting the compound of formula 3 with a compound of formula 4[(3R)—N-(t-butoxycarbonyl)-3-aminomethyl-piperidine] or formula 5[(3S)—N-(t-butoxycarbonyl)-3-aminomethyl-piperidine]

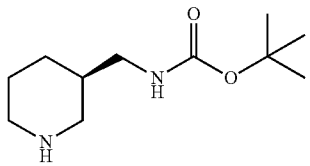
formula 4

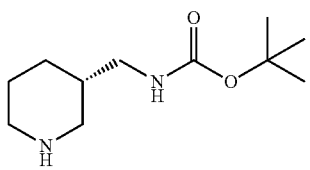
formula 5 in an aprotic solvent selected from a group consisting of dichloromethane, tetrahydrofuran, dioxane in presence of a coupling reagent selected from the group consisting of dicyclohexylcarbodiimide, benzotriazole-1-yl-oxy-tris-pyrrolidino-phosphonium hexafluorophophate, or an activating agent 1-hydroxy benzotrizole or isobutyl chloroformate at a temperature ranging between −20° C. to +30° C. for a period ranging from 1 to 3 hrs followed by purification using chromatography to produce the compound of formula 6 or 7 respectively.

3. The process as claimed in claim 2, wherein the compound of formula 3 is reacted with oxalyl chloride at 0° C. to obtain the acid chloride followed by reaction with compound of formula 4 or 5 in presence of triethylamine in dichloromethane to obtain the compound of formula 6 or 7 respectively.

4. The process as claimed in claim 2, wherein the compound of formula 3 is reacted with the compound of formula 4 or 5 in presence of a coupling reagent dicyclohexylcarbodiimide and 1-hydroxy benzotrizole in dichloromethane at a temperature ranging between −5° C. to 0° C. for a period ranging between 2 h to 3 h to obtain the compound of formula 6 or 7 respectively.

5. The process as claimed in claim 2, wherein the compound of formula 3 is reacted with compound of formula 4 or 5 in the presence of diisopropyl ethylamine, and benzotriazole-1-yl-oxy-tris-pyrrolidino-phosphonium hexafluorophophate, in dichloromethane at temperature ranging between −50° C. to 0° C. for a period ranging between 2 h to 3 h followed by stirring at temperature at a temperature ranging between 0° C. to 25° C. to obtain compound of formula 6 or 7 respectively.

6. The process as claimed in claim 2, wherein the compound of formula 3 is reacted with compound of formula 4 or 5 in presence of triethyl amine, and isobutyl chlorormate, in THF at −20° C., for a period ranging between 1 h to 2 h followed by stirring temperature ranging between 0° C. to 250° C. to obtain the compound of formula 6 or 7.

7. The process as claimed in claim 2 wherein the purification of the compound of formula 6 and 7 is carried out by crystallization using a solvent selected from the group consisting of pentane, hexane, cyclohexane, toluene and ethyl acetate.

8. A pharmaceutical composition comprising an antithrombotic effective amount of the compound of formula 6 or 7 with pharmaceutically acceptable additives and excipients.

9. The composition as claimed in claim 8 wherein the pharmaceutically acceptable additives are selected from the group consisting of DMSO, gum acacia or CMC, beta cyclodextrin, or any other pharmaceutically acceptable excipients.

10. Pure diastereomer compound of formula 6, (2S)-1-(4-methylphenylmethyl)-5-oxo-(3S)—{N-[(3-t-butoxycarbonyl aminomethyl)]-piperidin-1-yl}-pyrrolidine-2-carboxamide, having the structural formula:

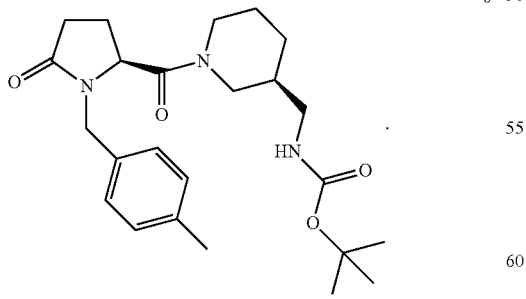

6

11. Pure diastereomer compound of formula 7, (2S)-1-(4-methylphenylmethyl)-5-oxo-(3R)—{N-[(3-t-butoxycarbonyl-aminomethyl)]-piperidin-1-yl}-pyrrolidine-2-carboxamide, having the structural formula:

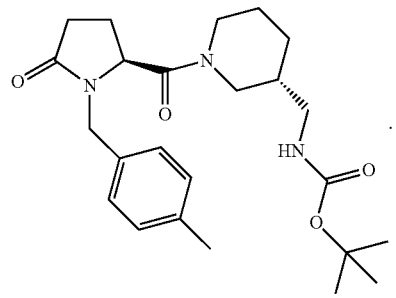

7

12. A process for the preparation of a compound of formula 6 wherein the process comprises the steps of:

a) reacting methyl pyroglutamate with p-methyl benzyl bromide in an aprotic solvent in presence of LiHMDS at a temperature ranging between 0 to 35° C. for a period ranging between 1 to 4 hr, quenching the reaction mixture with HCl and obtaining the compound of formula 2

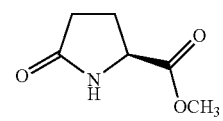

Methyl Pyroglutamic

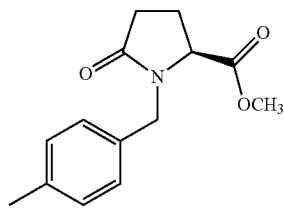

formula 2 b) reacting the compound of formula 2 with sodium carbonate at a temperature ranging between 0° C. to 30° C. for a period ranging between 0.5 to 4 hr to obtain 2S)—N-(p-methylphenylmethyl) pyroglutamic acid of formula 3; and,

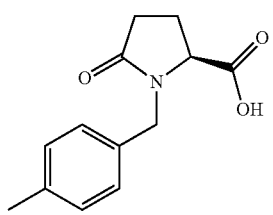

formula 3 c) reacting the compound of formula 3 with a compound of formula 4[(3R)—N-(t-butoxycarbonyl)-3-aminomethyl-piperidine] or formula 5[(3S)—N-(t-butoxycarbonyl)-3-aminomethyl-piperidine] in an aprotic solvent selected from a group consisting of dichloromethane, tetrahydrofuran, dioxane in presence of a coupling reagent selected from the group consisting of dicyclohexylcarbodiimide, benzotriazole-1-yl-oxy-tris-pyrrolidino-phosphonium hexafluorophophate, or an activating agent 1-hydroxy benzotrizole or isobutyl chloroformate at a temperature ranging between −20° C. to +30° C. for a period ranging from 1 to 3 hrs followed by purification using chromatography to produce compound of formula 6.

13. A process for the preparation of a compound of formula 7 wherein the process comprises:
   a) reacting methyl pyroglutamate with p-methyl benzyl bromide in an aprotic solvent in presence of LiHMDS at a temperature ranging between 0 to 35° C. for a period ranging between 1 to 4 hr, quenching the reaction mixture with HCl and obtaining the compound of formula 2

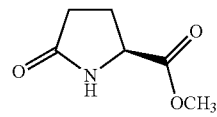

Methyl Pyroglutamic formula 2

b) reacting the compound of formula 2 with sodium carbonate at a temperature ranging between 0° C. to 30° C. for a period ranging between 0.5 to 4 hr to obtain 2S)—N-(p-methylphenylmethyl) pyroglutamic acid of formula 3; and formula 3

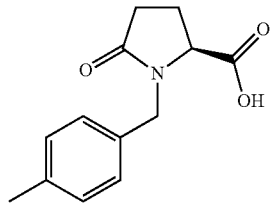

c) reacting the compound of formula 3 with a compound of formula 4[(3R)—N-(t-butoxycarbonyl)-3-aminomethyl-piperidine] or Formula 5[(3S)—N-(t-butoxycarbonyl)-3-aminomethyl-piperidine] in an aprotic solvent selected from a group consisting of dichloromethane, tetrahydrofuran, dioxane in presence of a coupling reagent selected from the group consisting of dicyclohexylcarbodiimide, benzotriazole-1-yl-oxy-tris-pyrrolidino-phosphonium hexafluorophophate, or an activating agent 1-hydroxy benzotrizole or isobutyl chloroformate at a temperature ranging between −20° C. to +30° C. for a period ranging from 1 to 3 hrs followed by purification using chromatography to produce compound of formula 6 or 7 respectively.

\* \* \* \* \*